(12) United States Patent
Hodak et al.

(10) Patent No.: US 12,036,419 B2
(45) Date of Patent: Jul. 16, 2024

(54) NEURAL INTERFACE DEVICE

(71) Applicant: Science Corporation, Alameda, CA (US)

(72) Inventors: Max Hodak, Alameda, CA (US); Alan Mardinly, Alameda, CA (US); Yifan Kong, Alameda, CA (US)

(73) Assignee: Science Corporation, Alameda, CA (US)

( * ) Notice: Subject to any disclaimer, the term of this patent is extended or adjusted under 35 U.S.C. 154(b) by 0 days.

(21) Appl. No.: 18/219,366

(22) Filed: Jul. 7, 2023

(65) Prior Publication Data

US 2024/0009481 A1 Jan. 11, 2024

Related U.S. Application Data

(60) Provisional application No. 63/438,947, filed on Jan. 13, 2023, provisional application No. 63/433,130, filed on Dec. 16, 2022, provisional application No. 63/359,100, filed on Jul. 7, 2022.

(51) Int. Cl.
| | |
|---|---|
| *G09G 3/32* | (2016.01) |
| *A61F 2/14* | (2006.01) |
| *A61K 35/30* | (2015.01) |
| *A61K 41/00* | (2020.01) |
| *A61N 5/06* | (2006.01) |

(52) U.S. Cl.
CPC .............. *A61N 5/0622* (2013.01); *A61F 2/14* (2013.01); *A61K 35/30* (2013.01); *A61K 41/00* (2013.01); *A61N 5/062* (2013.01); *G09G 3/32* (2013.01); *A61N 2005/0626* (2013.01); *A61N 2005/0652* (2013.01); *G09G 2320/0626* (2013.01)

(58) Field of Classification Search
CPC ................ A61F 2/14; A61F 2250/0001; A61F 2250/0002; G09G 3/32; G09G 2320/0626
See application file for complete search history.

(56) References Cited

U.S. PATENT DOCUMENTS

| | | |
|---|---|---|
| 9,518,980 B2 | 12/2016 | Looger et al. |
| 9,829,492 B2 | 11/2017 | Deisseroth et al. |
| 10,564,208 B1 | 2/2020 | Angle et al. |
| 10,935,776 B2 | 3/2021 | Waller et al. |
| 11,192,925 B2 | 12/2021 | Keravala |
| 11,592,654 B2 | 2/2023 | Waller et al. |

(Continued)

FOREIGN PATENT DOCUMENTS

| | | | | |
|---|---|---|---|---|
| CN | 113730029 B | * | 4/2022 | ............ A61F 2/141 |
| CN | 113730029 B | | 4/2022 | |

(Continued)

OTHER PUBLICATIONS

Translation of Chinese Patent Application CN-113730029B by Xu et al and published Apr. 26, 2022. (Year: 2022).*

(Continued)

*Primary Examiner* — Paul B Prebilic
(74) *Attorney, Agent, or Firm* — Jeffrey Schox; Diana Lin

(57) ABSTRACT

In variants, a neural interface system (e.g., retinal implant, neural implant, etc.) can include: a display, a controller, a power source, and/or any other suitable components. The system can be used with an external device including a communication element, a display-brain interface (e.g., cells), and/or any other suitable components.

13 Claims, 38 Drawing Sheets

(56) References Cited

U.S. PATENT DOCUMENTS

| | | | |
|---|---|---|---|
| 11,844,729 | B2* | 12/2023 | Saini .................. A61F 2/14 |
| 2009/0189830 | A1 | 7/2009 | Deering et al. |
| 2010/0152849 | A1 | 6/2010 | Degenaar et al. |
| 2013/0110236 | A1 | 5/2013 | Nirenberg |
| 2014/0101785 | A1 | 4/2014 | Looger et al. |
| 2016/0096036 | A1 | 4/2016 | Deisseroth et al. |
| 2018/0085018 | A1 | 3/2018 | Angle et al. |
| 2018/0173304 | A1 | 6/2018 | Lemoff et al. |
| 2019/0227490 | A1 | 7/2019 | Waller et al. |
| 2019/0256817 | A1 | 8/2019 | Gebhart et al. |
| 2020/0056299 | A1 | 2/2020 | Kong et al. |
| 2021/0007602 | A1 | 1/2021 | Seo et al. |
| 2021/0015604 | A1* | 1/2021 | Ma .................. A61F 2/1635 |
| 2021/0098341 | A1 | 4/2021 | Kong et al. |
| 2021/0239956 | A1 | 8/2021 | Waller et al. |
| 2022/0110681 | A1 | 4/2022 | Angle et al. |
| 2022/0118271 | A1 | 4/2022 | Deisseroth et al. |
| 2022/0201275 | A1 | 6/2022 | Klug et al. |
| 2023/0077899 | A1 | 3/2023 | Mardinly et al. |
| 2023/0147266 | A1 | 5/2023 | Mazaheripour et al. |
| 2024/0009481 | A1* | 1/2024 | Hodak .................. A61K 41/00 |

FOREIGN PATENT DOCUMENTS

| | | |
|---|---|---|
| EP | 3245292 B1 | 6/2021 |
| WO | 2017180482 A1 | 10/2017 |
| WO | 2017181068 A1 | 10/2017 |
| WO | 2018048742 A1 | 3/2018 |
| WO | WO-2024010916 A1 * | 1/2024 .............. A61F 2/14 |

OTHER PUBLICATIONS

Teo, Zhen Ling, et al., "Global Prevalence of Diabetic Retinopathy and Projection of Burden through 2045", Ophthalmology, Nov. 2021; 128(11):1580-1591.

Ahuja, A. K., et al., "Factors Affecting Perceptual Threshold in Argus II Retinal Prosthesis Subjects", Trans Vis Sci Tech., 2013;2(4):1, http://tvstjournal.org/doi/full/10.1167/tvst.2.4.1, doi:10.1167/tvst.2.4.1.

Al-Khersan, Hasenin, et al., "Innovative therapies for neovascular age-related macular degeneration", Expert Opinion on Pharmacotherapy, Jul. 12, 2019, https://doi.org/10.1080/14656566.2019.1636031.

Ambati, Jayakrishna, et al., "Age-Related Macular Degeneration: Etiology, Pathogenesis, and Therapeutic Strategies", Surv Ophthalmol 48 (3) May-Jun. 2003.

Ameline, B., et al., "Long-term expression of melanopsin and channelrhodopsin causes no gross alterations in the dystrophic dog retina", Gene Therapy (2017), 1-7, https://pubmed.ncbi.nlm.nih.gov/28880021/.

Aznauryan, Erik, et al., "Discovery and validation of human genomic safe harbor sites for gene and cell therapies", Cell Reports Methods 2, 100154, Jan. 24, 2022.

Barrese, James C., et al., "Scanning electron microscopy of chronically implanted intracortical microelectrode arrays in non-human primates", J Neural Eng. Apr. 2016 ; 13(2): 026003. doi:10.1088/1741-2560/13/2/026003.

Baumal, Caroline R., et al., "Efficacy and safety of brolucizumab in age-related macular degeneration: A systematic review of real-world studies", Acta Ophthalmologica. 2022;00:1-17, DOI: 10.1111/aos.15242.

Bi, Anding, et al., "Ectopic Expression of a Microbial-Type Rhodopsin Restores Visual Responses in Mice with Photoreceptor Degeneration", Neuron 50, 23e33, Apr. 6, 2006.

Busskamp, V., et al., "Optogenetic therapy for retinitis pigmentosa", Gene Therapy (2012) 19, 169-175.

Carpenter, R. H. S., et al., "Electrical Stimulation of the Human Eye in Different Adaptational States", J. Phyriol. (1972), 221, pp. 137-148.

Cehajic-Kapetanovic, Jasmina, et al., "Initial results from a first-in-human gene therapy trial on X-linked retinitis pigmentosa caused by mutations in RPGR", Nat Med 26, 354-359 (2020), https://doi.org/10.1038/s41591-020-0763-1.

Chaffiol, Antoine, et al., "A New Promoter Allows Optogenetic Vision Restoration with Enhanced Sensitivity in Macaque Retina", Molecular Therapy vol. 25 No. Nov. 11, 2017.

Choudhary, Mayur, et al., "Potential therapeutic targets for age-related macular degeneration: The nuclear option", Science Direct, Progress in Retinal and Eye Research, May 2023;94:101130. doi: 10.1016/j.preteyeres.2022.101130. Epub Oct. 8, 2022.

Dalkara, Deniz, et al., "In Vivo-Directed Evolution of a New Adeno-Associated Virus for Therapeutic Outer Retinal Gene Delivery from the Vitreous", Science Translational Medicine, Jun. 12, 2013 vol. 5 Issue 189 189ra76.

Dias, Marina Francs, et al., "Molecular genetics and emerging therapies for retinitis pigmentosa: Basic research and clinical perspectives", Progress in Retinal and Eye Research, Oct. 2017, 10.1016/j.preteyeres.2017.10.004.

Farah, Nairouz, et al., "Patterned Optical Activation of Retinal Ganglion Cells", Proceedings of the 29th Annual International Conference of the IEEE EMBS Cité Internationale, Lyon, France Aug. 23-26, 2007.

Fernandez, Eduardo, "Development of visual Neuroprostheses: trends and challenges", Bioelectronic Medicine (2018) 4:12, https://doi.org/10.1186/s42234-018-0013-8.

Finn, Avni P., et al., "Argus II retinal prosthesis system: a review of patient selection criteria, surgical considerations, and post-operative outcomes", Clinical Ophthalmology 2018:12 1089-1097.

Friedman, David S., et al., "Prevalence of Age-Related Macular Degeneration in the United States", Arch Ophthalmol. 2004;122:564-572.

Hartong, Dyonne T., et al., "Retinitis pigmentosa", Lancet 2006; 368: 1795-809.

Hebel, R., et al., "Size and Distribution of Ganglion Cells in the Human Retina", Anat Embryol (1983) 168:125-136.

Humayun, Mark S., et al., "Interim Results from the International Trial of Second Sight's Visual Prosthesis", Ophthalmology. Apr. 2012 ; 119(4): 779-788. doi:10.1016/j.ophtha.2011.09.028.

Humayun, Mark S., et al., "Pattern electrical stimulation of the human retina", Vision Research 39 (1999) 2569-2576.

Jones, Bryan W., et al., "Retinal Remodeling and Metabolic Alterations in Human AMD", Frontiers in Cellular Neuroscience, Apr. 2016, vol. 10, Article 103.

Kim, Ungsoo Samuel, et al., "Retinal Ganglion Cells—Diversity of Cell Types and Clinical Relevance", Frontiers in Neurology, published May 21, 2021.

Kling, A., et al., "Probing Computation in the Primate Visual System at Single-Cone Resolution", Annu Rev Neurosci. Jul. 8, 2019; 42: 169-186. doi:10.1146/annurev-neuro-070918-050233.

Kwak, Jay Jiyong, et al., "Short-Term Outcomes of the First in Vivo Gene Therapy for RPE65-Mediated Retinitis Pigmentosa", Yonsei Med J Jul. 2022;63(7):701-705, https://doi.org/10.3349/ymj.2022.63.7.701.

Lin, Bin, et al., "Retinal Ganglion Cells are Resistant to Photoreceptor Loss in Retinal Degeneration", PLoS One 8(6), published Jun. 28, 2013, doi:10.1371/journal.pone.0068084.

Luo, Yvonne H-L., et al., "Long-term Repeatability and Reproducibility of Phosphene Characteristics in Chronically Implanted Argus II Retinal Prosthesis Subjects", Am J Ophthalmol. Oct. 2016; 170:100-109. doi: 10.1016/j.ajo.2016.07.021. Epub Aug. 1, 2016.

Loudin, J D, et al., "Optoelectronic retinal prosthesis: system design and performanceJ. Neural Eng. 4 (2007) S72-S84", J. Neural Eng. 4 (2007) S72-S84.

Lu, Qi, et al., "Comparison of AAV-Mediated Optogenetic Vision Restoration between Retinal Ganglion Cell Expression and ON Bipolar Cell Targeting", Mol Ther Methods Clin Dev. May 22, 2020;18:15-23. doi: 10.1016/j.omtm.2020.05.009. eCollection Sep. 11, 2020.

McGregor, Juliette E., et al., "Optogenetic restoration of retinal ganglion cell activity in the living primate", Nature Communication, (2020) 11:1703, https://doi.org/10.1038/s41467-020-15317-6,www.nature.com/naturecommunications.

Medeiros, Nancy E., et al., "Preservation of Ganglion Cell Layer Neurons in Age-Related Macular Degeneration", Investigative Ophthalmology & Visual Science, Mar. 2001, vol. 42, No. 3.

(56) References Cited

OTHER PUBLICATIONS

Meng, Da, et al., "Therapy in Rhodopsin-Mediated Autosomal Dominant Retinitis Pigmentosa", Mol Ther. Jul. 6, 2022;30(7):2633. doi: 10.1016/j.ymthe.2022.06.007. Epub Jun. 16, 2022.
Muqit, Mahiul M. K., et al., "PRIMA subretinal wireless photovoltaic microchip implantation in non-human primate and feline models", PLOS On, https://doi.org/10.1371/journal.pone.0230713, Apr. 8, 2020.
Palanker, Daniel, et al., "Photovoltaic Restoration of Central Vision in Atrophic Age-Related Macular Degeneration", Ophthalmology, vol. 127, No. 8, Aug. 2020.
Raos, B. J., et al., "Selective PEGylation of Parylene- C/SiO2 Substrates for Improved Astrocyte Cell Patterning", Nature.com, Scientific Reports vol. 8, Article No. 2754 (2018).
Raz-Prag, Dorit, et al., "Electrical stimulation of different retinal components and the effect of asymmetric pulses", Journal of Neuroscience Methods 291 (2017) 20-27.
Sekirnjak, Chris, et al., "High-Resolution Electrical Stimulation of Primate Retina for Epiretinal Implant Design", The Journal of Neuroscience, Apr. 23, 2008, 28(17):4446-4456.
Sengupta, Abhishek, et al., "Red-shifted channelrhodopsin stimulation restores light responses in blind mice, macaque retina, and human retina", EMBO Molecular Medicine vol. 8 | No. 11 | 2016.
Soltan, Ahmed, et al., "High density µLED array for retinal prothesis with a eye-tracking system", 2016 IEEE Biomedical Circuits and Systems Conference (BioCAS).
Stingl, Katarina, et al., "Artificial vision with wirelessly powered subretinal electronic implant alpha-IMS", Proc R Soc B 280: 20130077, http://dx.doi.org/10.1098/rspb.2013.0077.
Tochitsky, Ivan, et al., "Restoring Visual Function to Blind Mice with a Photoswitch that Exploits Electrophysiological Remodeling of Retinal Ganglion Cells", Neuron, vol. 81, Issue 4, P800-813, Feb. 19, 2014.
Wang, Bing-Yi, et al., "Electronic photoreceptors enable prosthetic visual acuity matching the natural resolution in rats", Nature Communications, published Nov. 4, 2022, https://doi.org/10.1038/s41467-022-34353-y.
Ye, Jang Hee, et al., "Retinal Ganglion Cell (RGC) Responses to Different Voltage Stimulation Parameters in rd1 Mouse Retina", 32nd Annual International Conference of the IEEE EMBS Buenos Aires, Argentina, Aug. 31-Sep. 4, 2010.
"Optogenetics", Wikipedia, https://en.wikipedia.org/wiki/Optogenetics, downloaded May 16, 2022.
Chen, H. Isaac, et al., "Transplantation of Human Brain Organoids: Revisiting the Science and Ethics of Brain Chimeras", Cell Stem Cell. Oct. 3, 2019; 25(4): 462-472. doi:10.1016/j.stem.2019.09.002.
De Silva, Samantha R., et al., "Optogenetic approaches to therapy for inherited retinal degenerations", J Physiol. Nov. 1, 2022; 600(21): 4623-4632. Published online Aug. 17, 2022. doi: 10.1113/JP282076.
Gauvain, Gregory, et al., "Optogenetic therapy: high spatiotemporal resolution and pattern discrimination compatible with vision restoration in non-human primates", Communication Biology, (2021) 4:125, published Jan. 27, 2021, https://doi.org/10.1038/s42003-020-01594-w, www.nature.com/commsbio.
Kishi, Koichiro E., et al., "Structural basis for channel conduction in the pump-like channelrhodopsin ChRmine", Cell 185, 672-689, Feb. 17, 2022.
Petoe, Matthew A., et al., "A Second-Generation (44-Channel) Suprachoroidal Retinal Prosthesis: Interim Clinical Trial Results", Transl Vis Sci Technol. 2021; 10(10):12, https://doi.org/10.1167/tvst.10.10.12, published Aug. 12, 2021.
Xu, Huizhuo, et al., "First Human Results With the 256 Channel Intelligent Micro Implant Eye (IMIE 256)", Transl Vis Sci Technol. 2021;10(10):14, https://doi.org/10.1167/tvst.10.10.14, published online Oct. 27, 2021.
Mardinly, Alan R., et al., "Precise multimodal optical control of neural ensemble activity", Nat Neurosci. Jun. 2018; 21(6): 881-893.
Sridharan, Savitha, et al., "High-performance microbial opsins for spatially and temporally precise perturbations of large neuronal networks", Neuron 110, 1139-1155 Apr. 6, 2022.

\* cited by examiner

*array of display units*

| μLED and driver | μLED and driver | μLED and driver |
|---|---|---|
| μLED and driver | μLED and driver | μLED and driver |
| μLED and driver | μLED and driver | μLED and driver |

FIGURE 8A

*array of display units*

| μLED and driver | μLED and driver | μLED and driver |
|---|---|---|
| μLED and driver | electrode | μLED and driver |
| μLED and driver | μLED and driver | μLED and driver |

FIGURE 8B

NEURAL INTERFACE DEVICE

CROSS-REFERENCE TO RELATED APPLICATIONS

This application claims the benefit of U.S. Provisional Application No. 63/359,100 filed 7 Jul. 2022, U.S. Provisional Application No. 63/433,130 filed 16 Dec. 2022, and U.S. Provisional Application No. 63/438,947 filed 13 Jan. 2023, each of which is incorporated in its entirety by this reference.

TECHNICAL FIELD

This invention relates generally to the neural interface field, and more specifically to a new and useful system and method in the neural interface field.

BRIEF DESCRIPTION OF THE FIGURES

FIGS. 8A and 8B depict examples of sets of display units.

DETAILED DESCRIPTION

The following description of the embodiments of the invention is not intended to limit the invention to these embodiments, but rather to enable any person skilled in the art to make and use this invention.

1. Overview

Figure 1:
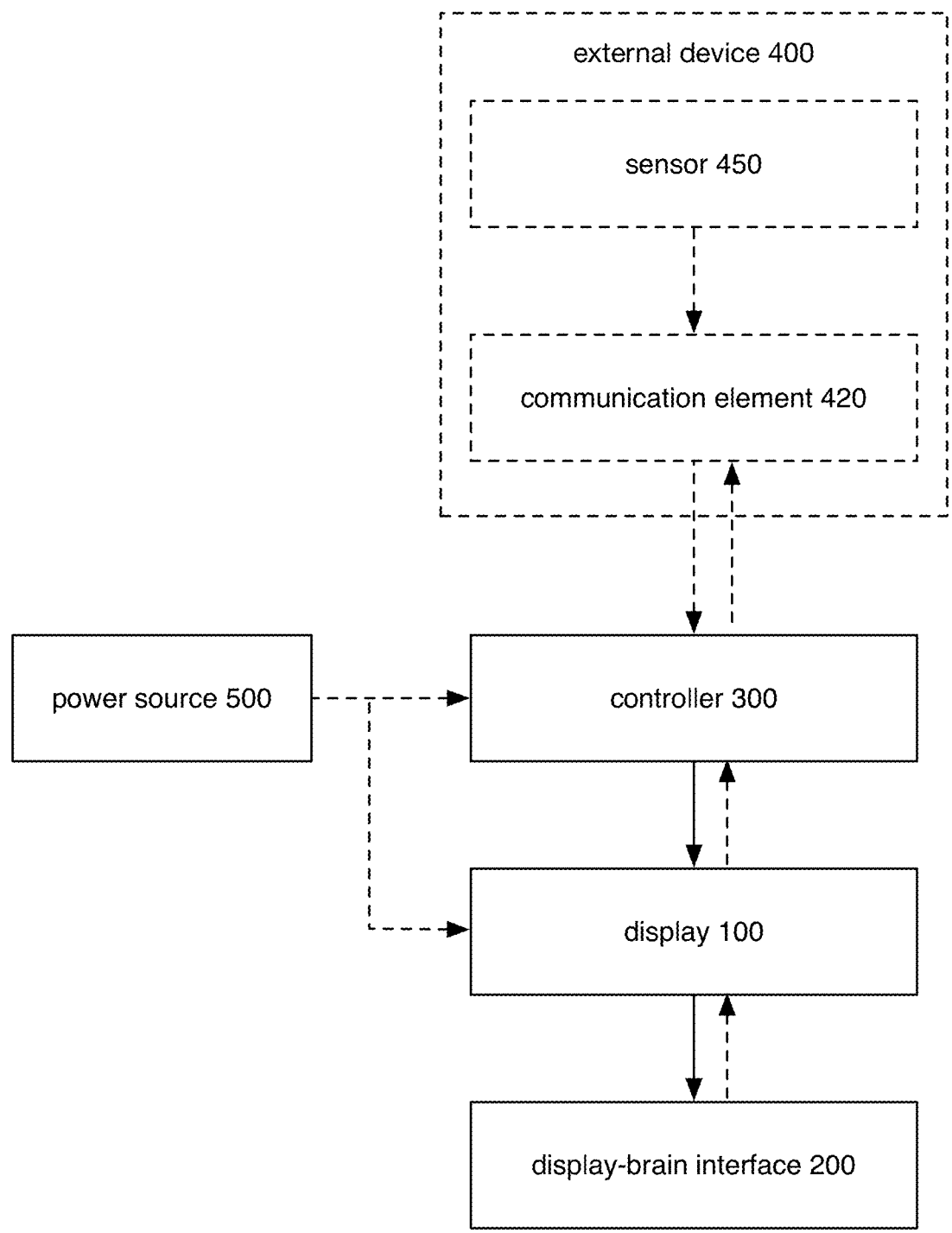
FIG. 1 is a schematic representation of a variant of the system.

As shown in FIG. 1, the system can include: a display 100, a controller 300, and a power source 500. The system can be used with an external device 400, a display-brain interface 200, and/or other components. However, the system can additionally or alternatively include any other suitable components.

In variants, the system can function to transmit information to a user's brain. In a first example, the system (e.g., a retinal implant) can function as a visual prosthesis to restore vision for users who have lost function of all or some of their photoreceptors (e.g., degenerated and/or otherwise impaired photoreceptors), ganglia, and/or other sensory cells. In a second example, the system (e.g., a neural implant) can function to provide stimulation to the brain to restore and/or augment one or more senses a user.

2. Examples

In an example, a display is embedded in-situ (e.g., in the eye, brain, ear, brain stem, muscle, arm, etc.). The display emits an excitation signal (e.g., one or more wavelengths of light), wherein recipient cells produce a biochemical signal in response to detecting the excitation signal. The biochemical signal can be interpreted as data (e.g., by the brain). The data presented by the display (via the excitation signals) can be determined based on an input (e.g., images sampled by a camera, an artificial reality engine, etc.) transmitted to a controller, wherein the controller is connected to the display. The recipient cells are preferably genetically modified to express transgenic proteins sensitive to the excitation signal (e.g., sensitive to a wavelength of light) emitted by the display, wherein the modified cells stimulate neurons in the brain responsive to light activation. The brain can then interpret the stimulation to enable the user to "see" the content. Alternatively, the cells can be unmodified or otherwise genetically modified. The recipient cells can be eye cells (e.g., retinal ganglion cells, etc.), neurons, somatic cells, and/or any other cell type.

3. Technical Advantages

Variants of the technology can confer one or more advantages over conventional technologies.

First, variants of the technology can restore and/or augment one or more senses of a user (e.g., restoring sight in users with blindness). In some diseases like retinitis pigmentosa and macular degeneration, the photoreceptors are damaged while the cells of the optic nerve, the retinal ganglion cells (RGCs), remain functional. Variants of the technology can stimulate the ganglion cells directly, which can restore visual input to the brain without replacing the photoreceptors. In a specific example, the system includes an optogenetic visual prosthesis that stimulates genetically modified cells transfected with a gene for a light-sensitive protein (e.g., an opsin).

Second, conventional methods of interfacing with neurons require large capacitive electrode systems with cumbersome hermetic feedthroughs (to seal implanted electrodes). In variants, this technology can provide content to the brain (e.g., via RGCs, via neurons, etc.) using a display implant that has a higher resolution (e.g., a 1:1 mapping of cells to light emission systems on the display), a higher number of signal elements, and/or a smaller form factor with fewer or no hermetic feedthroughs. In an example, variants of the technology can be scalable (e.g., to thousands of pixels, to hundreds of thousands of pixels, etc.), enabling an implantable visual prosthesis capable of generating vision by stimulating RGCs at or near cellular resolution.

Third, variants of the technology can include manufacturing an implanted neural interface device (e.g., including a display, display-controller connector, and controller) that can better conform to the eye, decreasing mechanical stress during and after implantation. In a first example, the neural interface device can be manufactured using monolithic integration on a multilayer thin film, which can have increased flexibility. In a second example, the neural interface device can be manufactured with a three-dimensional (3D) geometry. In a specific example, the device is manufactured using a multilayer film with a sacrificial layer that is dissolved to reveal the 3D geometry including a first flap (housing the controller) that can be implanted on the outer surface of the eye and a second flap (housing the display) that can be implanted inside the eye on the retina. In a third example, no flap may be needed and the device bends into the eye.

Fourth, the diversity of coding schemes present in distinct RGC subtypes can present a problem for visual prosthetics. Numerous classes of RGCs can exist in the retina, each of which can carry distinct information, such as ON and OFF RGCs that increase firing rate with increased or decreased luminance, respectively. Each RGC type can contribute to the reconstruction of visual stimuli, and neighboring RGCs can encode different aspects of visual stimuli. Variants of the technology can provide the advantage of addressing RGCs at or near cellular resolution using an advanced visual prosthesis for photoreceptor degeneration. In a specific example, an approach to vision restoration can include optogenetic stimulation of RGCs using an implantable thin film PLED display with pixels approximately the size of RGC somas such that the display (e.g., functioning as an implanted optogenetic therapy) operates at or near cellular resolution.

Fifth, variants of the technology can use an active driver for the display (e.g., including a thin-film transistor backplane), which can increase the frame rate when taken in conjunction with the minimum times that can reliably elicit optogenetically-evoked action potentials at one or more light levels (e.g., light levels below a safety threshold). In examples, driver electronics can be placed inside the eye (e.g., for an active display with more pixels). This could allow for a large reduction in the number of wires routed through the sclera, which could in turn allow more flexible positioning of the device. This can also allow for less power to be consumed and/or transmitted through the eye, between the controller 300 and the display 100, since the controller only needs to signal state changes instead of constantly driving the display. Additional examples include the integration of thin film transistors directly on each pixel, and/or a CMOS device with microLEDs directly bonded to it.

Sixth, increasing the coverage on the retina may grant access to more of the visual field. In examples, larger displays can be unfolded inside the eye during surgery (e.g., to account for surgical constraints on the scleral incision size).

Seventh, variants of the system can achieve optogenetic control of the peripheral retina using a display with stimulation pixels roughly matched in size and pitch to the density of RGCs. Achieving single-cell resolution with 1-photon optogenetic excitation in vivo can be extremely challenging without complex optics because of significant axial light propagation. This problem of axial resolution can be obviated in the peripheral retina, where RGCs can be arrayed in a monolayer. In the perifoveal region, where RGCs can be stacked in layers up to 10 cells deep, axial light propagation may decrease resolution, but sparse viral transfection could limit the number of off-target RGC activations.

Eighth, in variants, an implanted retinal display has several advantages compared to optical stimulation from outside the eye. Stimulation from goggles can contend with both macro and microscopic movement of the goggles relative to the eye, rapid changes in eye position, and variable pupil diameter, which affects the numerical aperture of the system. Stimulating RGCs with at or near single-cell precision and millisecond resolution from outside the eye can require extremely low-latency closed-loop tracking and computation, which can be difficult to implement. In contrast, an implanted display can feature a fixed mapping between a given pixel and a specific RGC or set of RGCs. In variants, the display can move with the eye, eliminating the need to dynamically correct stimulation patterns. For example, while eye tracking can be used to render a scene on the implant, the stimulation pattern does not need to dynamically track a moving target.

Ninth, in variants, an implanted display can be more efficient in terms of pixel use: for an augmented reality display, a visual scene can be rendered in high definition across the entire field of view, since the eye may saccade to any part of the visual scene. In contrast, an implanted display's resolution can degrade concentrically away from the fovea to match the density of RGCs. This distinction can be used in designing an implant that takes advantage of retinal coding principles: a display that renders an entire visual scene may not know before a saccade which RGCs it will address, so the encoding potential of the prosthesis can be limited. Finally, a stable mapping of pixels to cells using an implanted display may help with plasticity even in the case of poor encoding, since downstream structures can receive consistently patterned input.

However, further advantages can be provided by the system and method disclosed herein.

4. System

Figure 6:
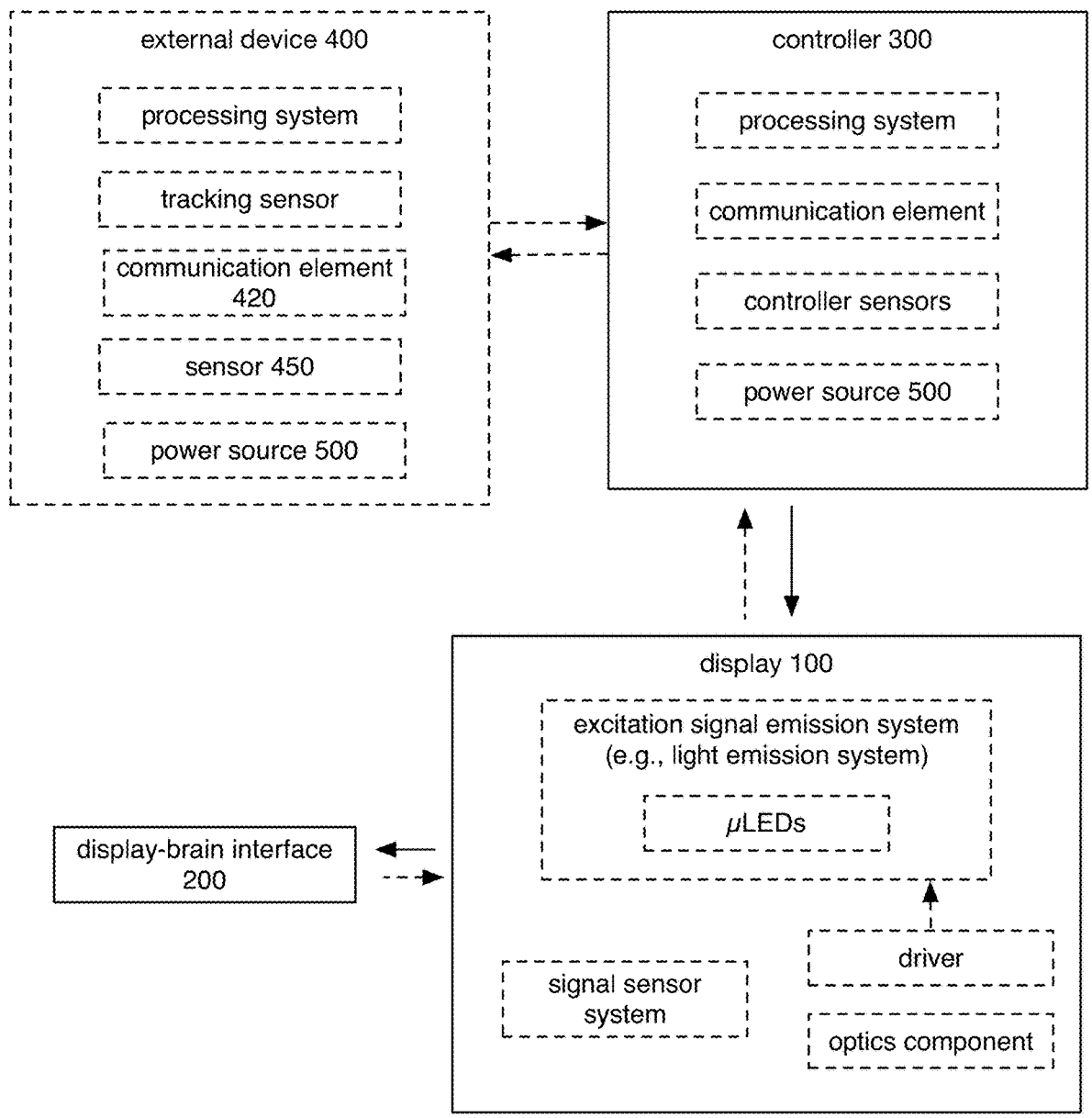
FIG. 6 is a schematic representation of an example of the system.
Figure 7A:
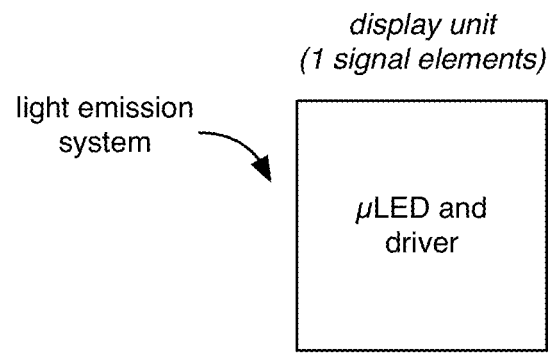
FIGS. 7A, 7B, and 7C depict examples of a display unit.
Figure 7B:
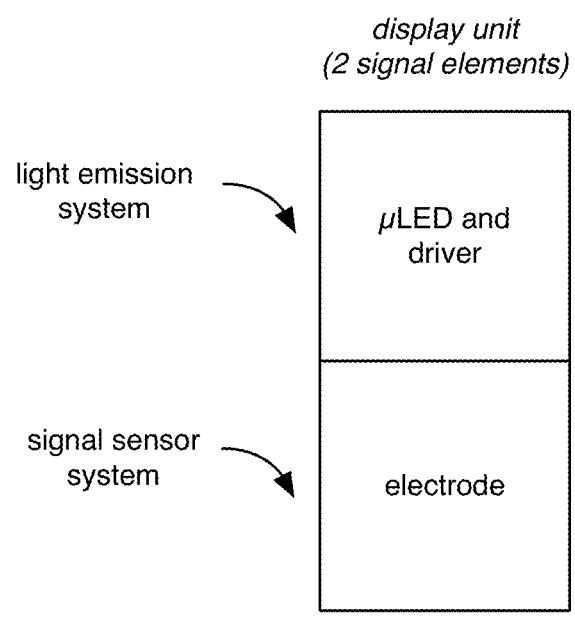
Figure 7C:
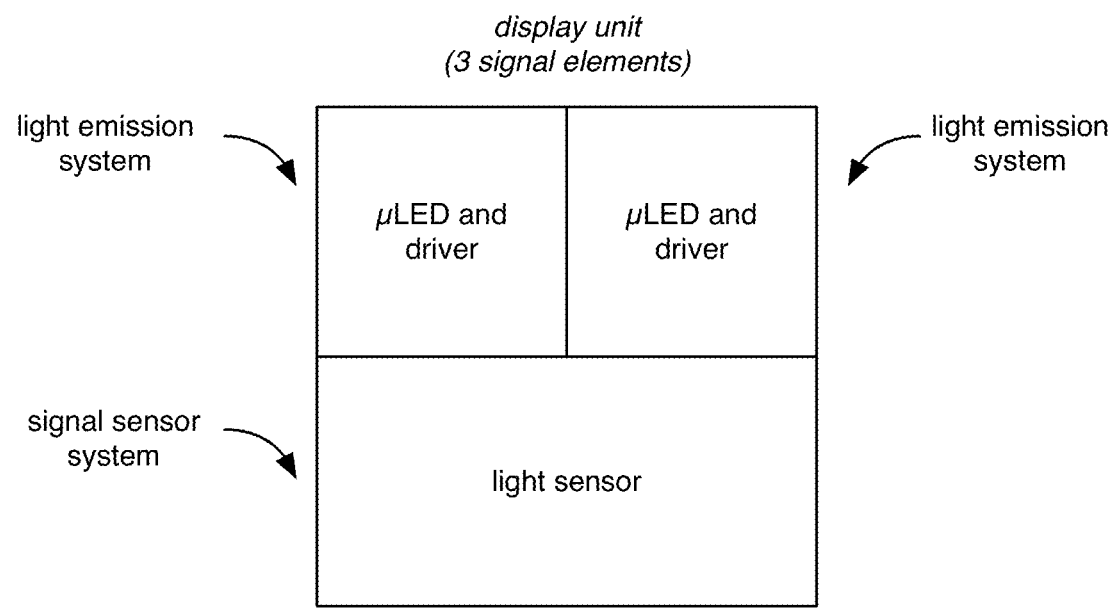
Figure 9:
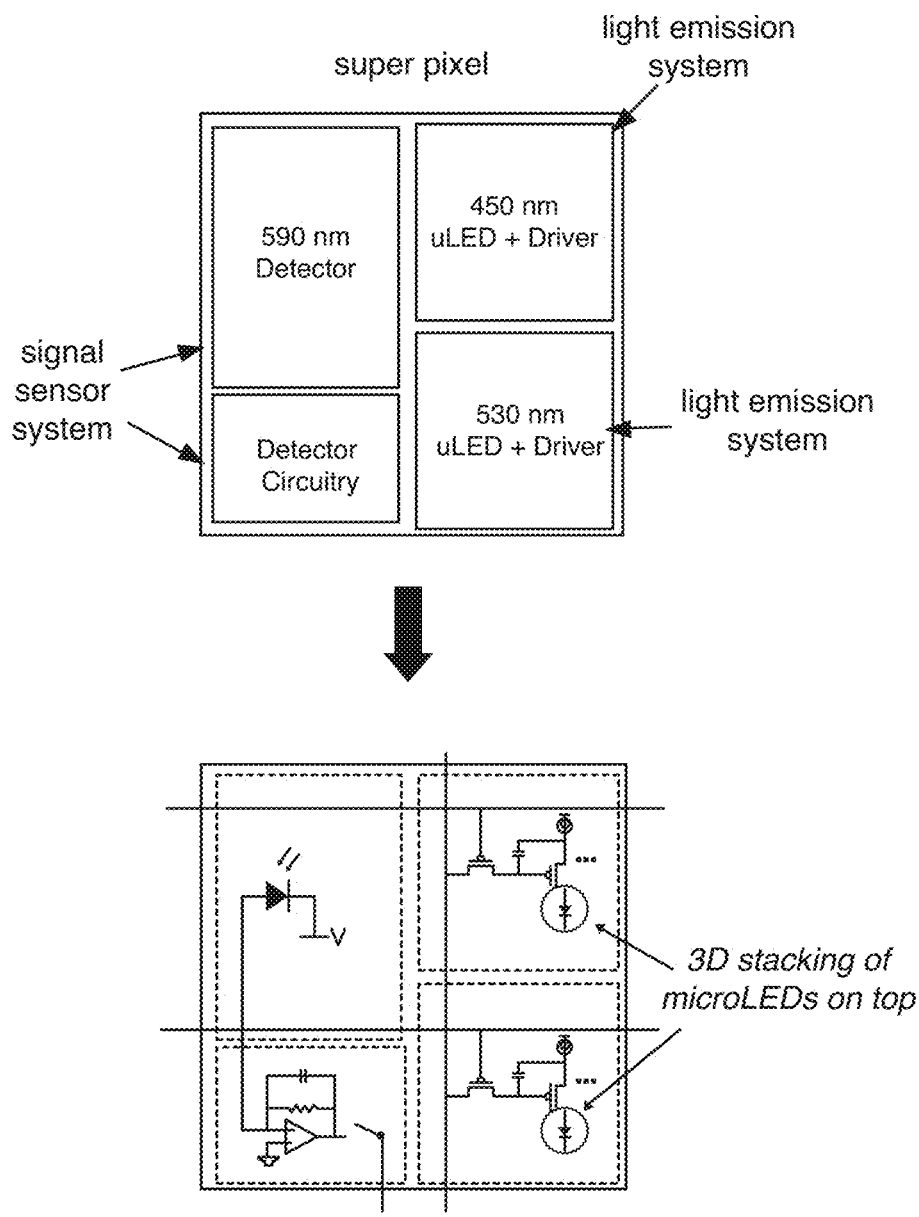
FIG. 9 depicts an illustrative example of a display 'super pixel.'

As shown in FIG. 1, the system can include: a display 100, a controller 300, and a power source 500. Optionally, the system can include a display-controller connector, a display-brain interface 200 and/or any other suitable component. The system can be used with an external device 400. An example is shown in FIG. 6.

One or more components of the system (e.g., one or more components of the display 100) are preferably partially or fully transparent, but can alternatively be translucent, opaque, or have any other suitable optical characteristics. One or more components of the system are biocompatible and/or are encapsulated in a biocompatible, but can alternatively be not biocompatible and/or otherwise configured.

The system is preferably an implant, but can additionally or alternatively include a non-implanted device and/or be otherwise configured. In examples, one or more components of the system is implanted in or on: the eye (e.g., retina, sclera, etc.), brain, brain stem, spinal cord, ear, muscle, skin, at or near a nerve, and/or any other body region of a user. The user can be a human, an animal (e.g., rabbit), and/or any other organism. When the system is an implant, one or more components of the system can be retained in situ by: tissue adhesives, via extrusions (e.g., 'spikes') that act as anchors, tacks (e.g., through tack holes in the device), sutures, by inducing fibrotic growth around or through the components (e.g., fenestration holes in the components can enable fibrotic growth to secure the component), and/or using any other method.

The display 100 (e.g., a photonic interconnect) functions to emit excitation signals that are received by cells (e.g., cells within the display-brain interface 200), wherein the signals can encode content (e.g., visual data, sensory data, other external information, artificial data, any other data, etc.). Additionally or alternatively, the display 100 can function to measure a cell state. The cells can be genetically modified cells (e.g., cells with optogenetic actuators and/or optogenetic sensors, hypoimmune cells, etc.) and/or non-genetically modified cells.

Figure 15:
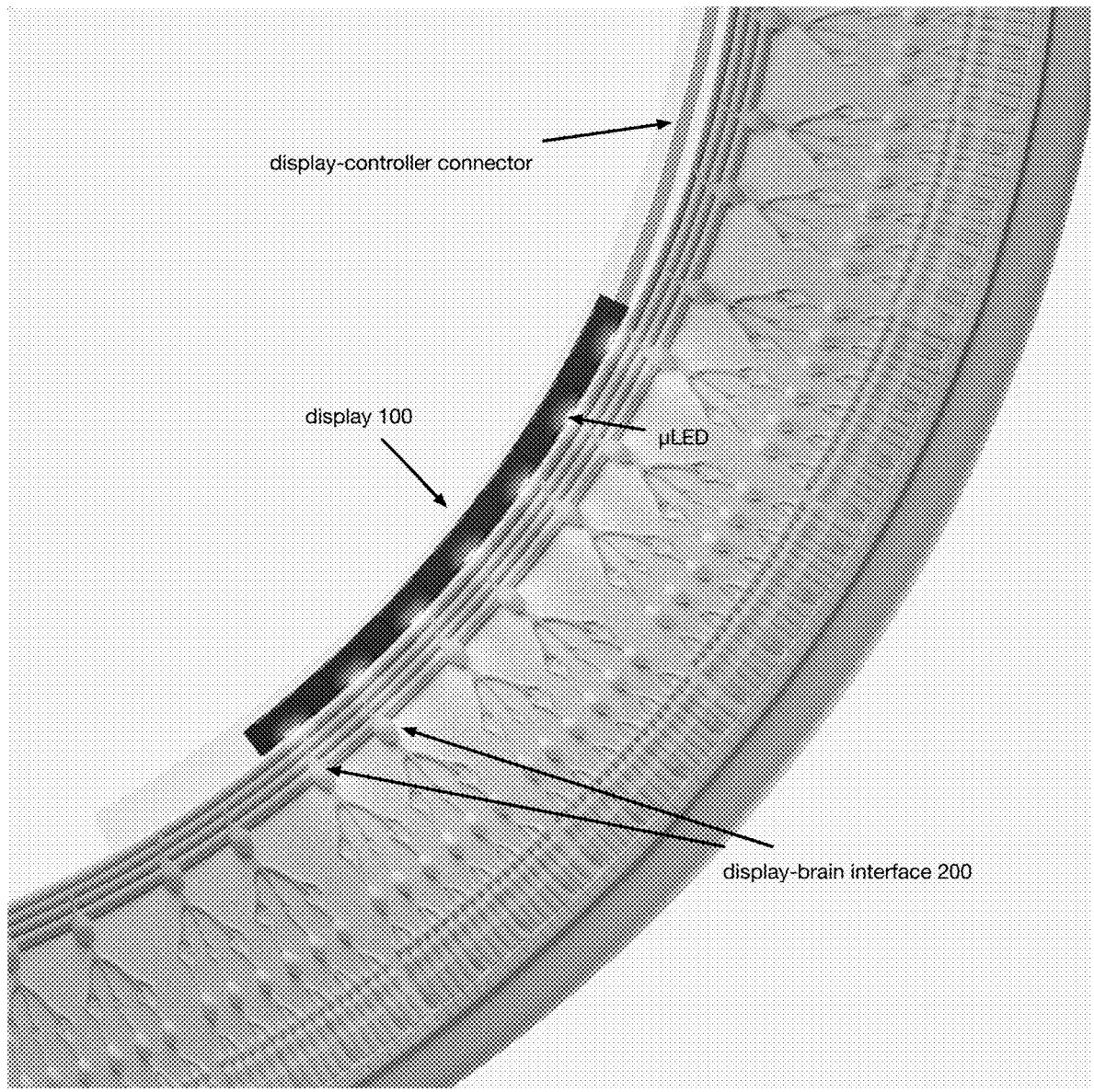
FIG. 15 depicts an illustrative example of an implanted display.

The display 100 can be implanted at an implantation location. Examples of implantation locations include: the retina (e.g., macula, peripheral retina, across all or a portion of both the macula and the peripheral retina, etc.; on the internal limiting membrane of the retinal surface), the optic nerve (e.g., aligned with the optic nerve), the brain (e.g., the visual cortex, the motor cortex, etc.; within the brain interior, on the brain surface, a combination thereof, etc.), the brain stem, spinal cord, ear (e.g., ear canal), muscle, skin, at or near a nerve, and/or any other location associated with a user. In a specific example, the display 100 (and optionally the display-controller connector) can be an intraocular component of the system. An example is shown in FIG. 15.

The display 100 can be connected to the display-controller connector, the controller 300 (e.g., wirelessly connected, connected via the display-controller connector, etc.), and/or any other system component. The display 100 can include one or more excitation signal emission systems (e.g., light emission systems) including circuitry and/or components configured to emit signals (e.g., light) based on controls received from the controller 300 (e.g., via the display-controller connector). The control instructions (e.g., display instructions) can include emission parameters and/or any other display instructions. The display 100 can optionally include one or more signal sensor systems configured to measure a cell state, wherein the cell state can optionally be transmitted to the controller 300 (e.g., via the display-controller connector). In a specific example, the signal sensor systems include sensors to measure signals emitted by cells (e.g., protein fluorescence spatiotemporal parameters, intensity, ions, voltage, current, etc.). The display can optionally include one or more integrated circuits, optics components, and/or any other suitable components.

Figure 14:
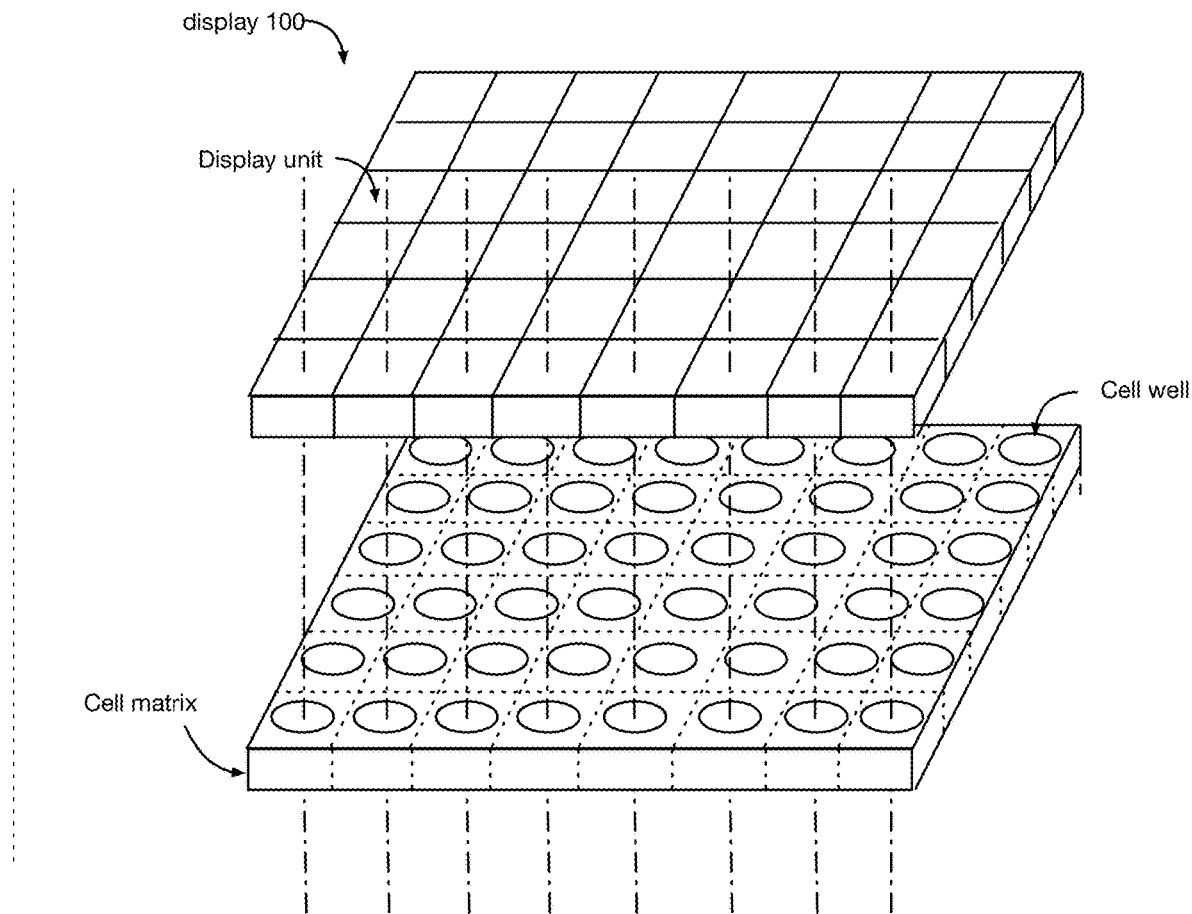
FIG. 14 depicts an illustrative example of a display aligned with a cell matrix.

The display 100 can include a set of display units. A display unit can be: a pixel (e.g., with one signal element), a super pixel (e.g., with multiple signal elements), and/or otherwise configured. Examples are shown in FIG. 7A, FIG. 7B, FIG. 7C, and FIG. 9. A signal element can be an excitation signal emission system, a signal sensor system, and/or any other signal component. The mapping between display units and cells can be 1:1 (e.g., one display unit each cell with an optogenetic actuator; one display unit for one cell having both optogenetic actuators and optogenetic sensors; etc.; example shown in FIG. 14), 1:2 (e.g., one display unit for two cells: one cell with an optogenetic actuator and one cell with an optogenetic sensor), randomly determined, unconstrained, a variable mapping across the display (e.g., an increased ratio between display units and cells further from the fovea), and/or have any other mapping. In a specific example, the display 100 can operate at or near cellular resolution (e.g., one display unit and/or signal element thereof can excite less than 20 cells, less than 10 cells, less than 5 cells, less than 2 cells, 1 cell, etc.). The display units in the set of display units can be the same or different from each other. In a first example, the display units are substantially the same (e.g., the same size, each with the same signal elements or set of signal elements); an example is shown in FIG. 8A. In a second example, the set of display units can include a first subset of display units (e.g., each having only an excitation signal emission system) that is different from a second subset of display units (e.g., each having a signal sensor system; each having a signal sensor system and an excitation signal emission system; etc.); the number of display units in the first subset can be larger, smaller, or the same as the number of display units in the second subset. An example is shown in FIG. 8B.

Figure 26:
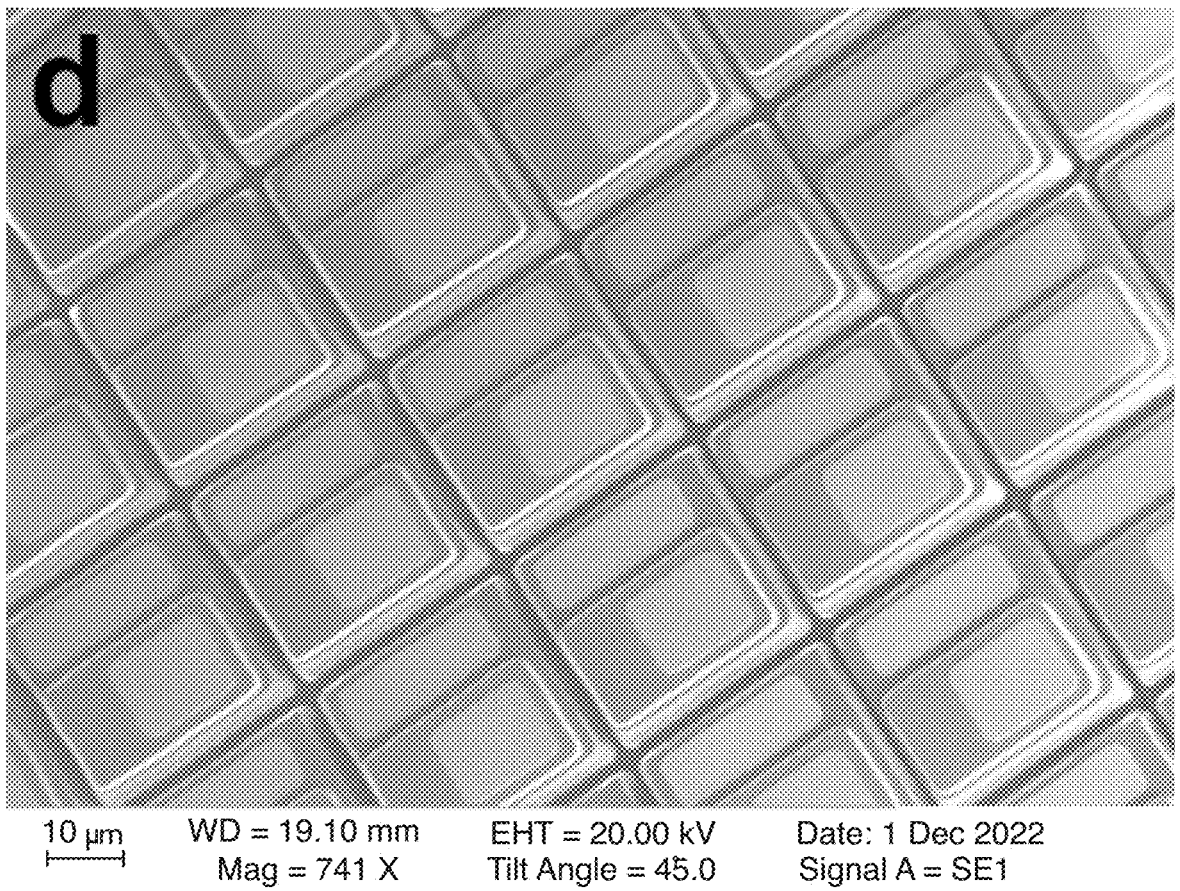
FIG. 26 is a scanning electron microscope image of a display.

The number of display units can be between 100-50,000 or any range or value therebetween (e.g., at least 1000; at least 2000; at least 5000; at least 10000; 2048; 4096; 8192; 16000; etc.), but can alternatively be less than 100 or greater than 50,000. All or a portion of the display units can be functional (e.g., connected to the controller via the display-controller connector). In an example, only a portion of the display units are connected to the controller to reduce the number of connections in the display-controller connector. The percentage of functional display units out in the set of display units can be between 20%-100% or any range or value therebetween (40%-90%, 50%, less than 90%, less than 80%, less than 70%, etc.), but can alternatively be less than 20%. In a first illustrative example, 8,192 display units are functional out of 16,000 total display units. In a second illustrative example, 2,048 display units are functional out of 4,096 total display units. The resolution of the set of display units can be between 100-5,000 display units per mm$^2$, or any range or value therebetween (greater than 500 display units per mm$^2$, greater than 1000 display units per mm$^2$, greater than 2000 display units per mm$^2$, etc.), but can alternatively be less than 100 display units per mm$^2$ or greater than 5,000 display units per mm$^2$. The resolution of display units can be the same across the display or vary across the display (e.g., an increased resolution of display units or of functional display units towards the fovea of the retina). The diameter of a display unit and/or a signal element thereof can be between 1 μm-10 cm or any other range or value therebetween (e.g., less than 500 μm, less than 100 μm, less than 50 μm, less than 20 μm, less than 10 μm, less than 5 μm, 5 μm-100 μm, 10 μm-20 μm, 15 μm, etc.), but can alternatively be less than 1 μm or greater than 10 cm. An example is shown in FIG. 26. The emission area of each excitation signal emission element can be between 10 μm$^2$-10,000 μm$^2$ or any other range or value therebetween (e.g., less than 1000 μm$^2$, less than 500 μm$^2$, less than 100 μm$^2$, 50 μm$^2$-100 μm$^2$, 66 μm$^2$, 285 μm$^2$-680 μm$^2$, etc.), but can alternatively be less than 10 μm$^2$ or greater than 10,000 μm$^2$. The display unit pitch (e.g., center-to-center distance between display units) can be between 5 μm-10 cm or any range or value therebetween (e.g., less than 500 μm, less than 100 μm, less than 50 μm, 5 μm-100 μm, 20 μm, 42 μm, etc.), but can alternatively be less than 5 μm or greater than 10 cm.

The surface area of the display 100 (e.g., of the total display and/or of an active area of the display containing the set of display units) can be between 0.5 mm$^2$-50 cm$^2$ or any range or value therebetween (e.g., 2 mm$^2$-10 mm$^2$, 5 mm$^2$-10 mm$^2$, 7.29 mm$^2$, 6.55 mm$^2$, etc.), but can alternatively be less than 0.5 mm$^2$ or greater than 50 cm$^2$. The thickness of the display 100 (e.g., including an optional encapsulant, backing, and/or any other secondary material) can be between 2 μm-150 μm or any range or value therebetween (e.g., 20 μm-60 μm, 10 μm-30 μm, 20 μm, 22 μm, 30 μm, 40 μm, 50 μm, 60 μm, etc.), but can alternatively be less than 2 μm or greater than 150 μm. The display surface geometry can be a square, rectangle, circle, oval, and/or any other shape. The display 100 is preferably flexible, but can alternatively be rigid and/or have both flexible and rigid components.

Figure 10:
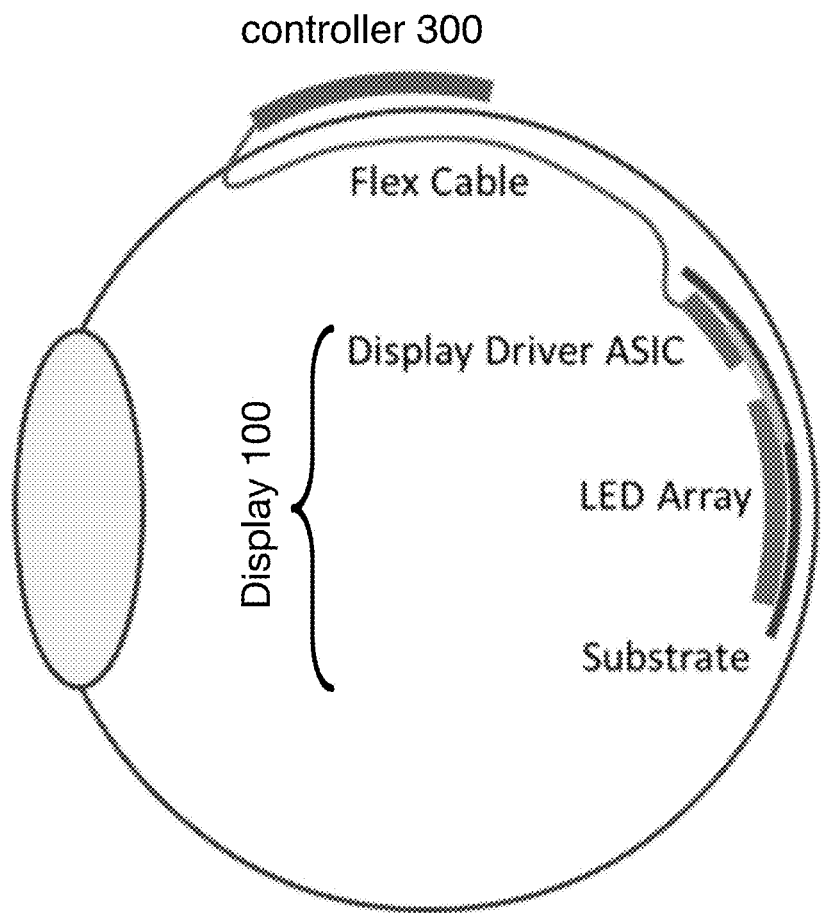
FIG. 10 depicts an example of the system including a driver.

The excitation signal emission system can be a light emission system, an electrical emission system (e.g., emitting a current signal and/or voltage signal), and/or any other signaling system. The light emission system preferably includes a μLED, but can additionally or alternatively include laser diodes (e.g., vertical-cavity surface-emitting laser, laser cavities, etc.), phosphors, and/or any other light emission system. In a specific example, phosphors can enable a wavelength shift of the light emission system and/or an emission lifetime shift (e.g., to better match the time constant of the cells in the display-brain interface 200). In an example, the light emission system can include a μLED (e.g., the display includes an array of μLEDs), wherein the driver for the μLEDs can be collocated with the μLEDs on the display 100 (e.g., within the corresponding display unit, adjacent to the corresponding display unit, adjacent to the set of display units, etc.), located adjacent to the display, located at the display-controller connector, located at the controller 300, and/or otherwise positioned. An example is shown in FIG. 10. In a first specific example, the driver can be a passive driver. In a second specific example, the driver can be an active driver (e.g., including an integrated circuit, transistors, other logic components, etc.) enabling the display 100 to include an active array of display units (e.g., an active array of μLEDs). The μLED material can include indium gallium nitride, gallium nitride (e.g., biocompatible gallium nitride), indium gallium phosphide, an organic emitter, and/or any other light emission materials. The μLEDs can be fabricated directly with the display (e.g., with the same traces; on the same wafer; etc.), be assembled onto a display backing and/or encapsulant after circuit fabrication, and/or otherwise manufactured.

Figure 27:
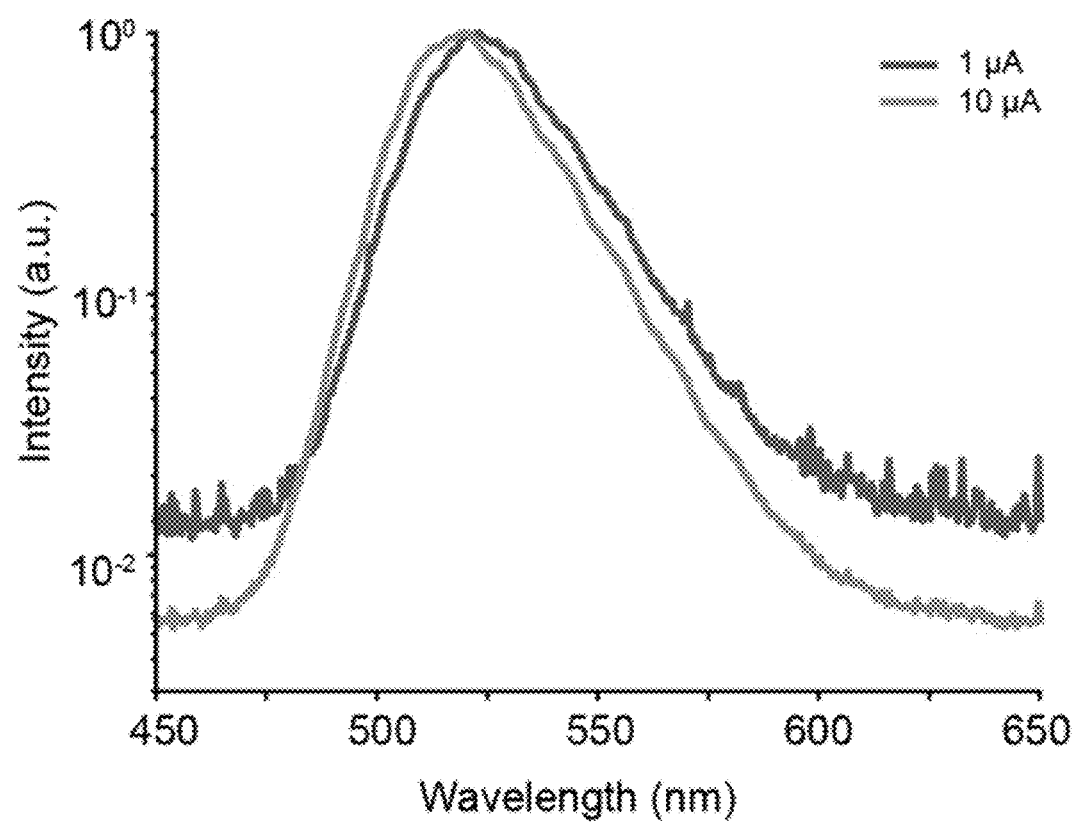
FIG. 27 depicts emission spectra of an example display at 1 µA and 10 µA.
Figure 28:
FIG. 28 is an image of a system implantation procedure, with the system (e.g., retinal implant) attached to a surgical carrier device.
Figure 29:
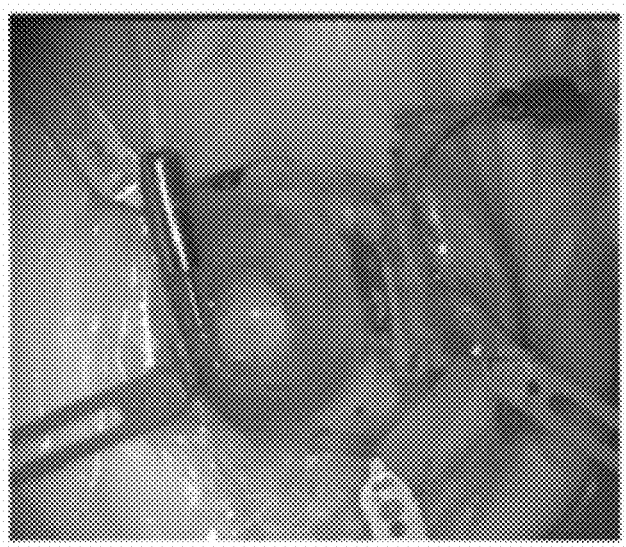
FIG. 29 is an image of the implantation procedure after the surgical carrier device is removed.

The light emission system can emit one or more wavelengths of light at one or more luminous flux levels. The luminous flux is preferably greater than or equal to a light activation threshold of an optogenetic actuator (e.g., an opsin) associated with cells in the display-brain interface 200, but can alternatively be less than a light activation threshold of the optogenetic actuator and/or have any other value. In examples, the luminous flux (and/or the irradiance received by a cell in the display-brain interface 200) is between 0.01 mW/cm$^2$-100 mW/cm$^2$ or any range or value therebetween (e.g., 0.1-20 mW/cm$^2$, greater than 5 mW/cm$^2$, greater than 10 mW/cm$^2$, greater than 20 mW/cm$^2$, greater than 30 mW/cm$^2$, greater than 50 mW/cm$^2$, less than 70 mW/cm$^2$, etc.), but can alternatively be less than 0.01 mW/cm$^2$ or greater than 100 mW/cm$^2$. The wavelength(s) preferably correspond to the excitation wavelengths of an optogenetic actuator (e.g., an opsin) associated with cells in the display-brain interface 200, but can alternatively not be associated with an optogenetic actuator (e.g., when the display 100 emits light onto healthy photoreceptors). The wavelength (e.g., spectral peak) can be between 400 nm-800 nm or any range or value therebetween (e.g., 510 nm-550 nm, between 530 nm-540 nm, 530 nm, 540 nm, 545 nm, 550 nm, 560 nm, 450 nm-485 nm, 500 nm-570 nm, 625 nm-750 nm, etc.), but can alternatively be less than 400 nm or greater than 800 nm. In a first example, the wavelength values correspond to red light only (e.g., between 625 nm-750 nm). In a second example, the wavelength values correspond to blue light only (e.g., between 450 nm-485 nm). In a third example, the wavelength values correspond to green light only (e.g., between 500 nm-570 nm). In a fourth example, the wavelength values correspond to red, blue, and/or green light (e.g., an RBG light display). In a specific example, the wavelength can not include red light (e.g., blue and/or green wavelengths are used) to reduce the photochemical hazard of the display 100. The full-width at half-maximum value of the light emission system can be between 5 nm-50 nm or any range or value therebetween (e.g., 20 nm), but can alternatively be less than 5 nm or greater than 50 nm. However, the display can emit light having any other wavelength, frequency, photon energy, intensity, flux, amplitude, and/or other parameter. An example is shown in FIG. 27. Additionally or alternatively, the display can emit non-light signals (e.g., haptic signals, acoustic signals, electrical signals, etc.).

The excitation signal emission systems can operate according to emission parameters (e.g., emission instructions) received from the controller 300, wherein the emission parameters encode content. Emission parameters can include spatial parameters (e.g., which display units to operate), temporal parameters (e.g., when to initiate signal emission, length of signal emission, etc.), intensity and/or amplitude parameters (e.g., intensity and/or amplitude of light), light wavelengths, and/or any other parameters defining the signals emitted by the excitation signal emission systems. For example, the emission parameters can prescribe a timeseries of light array patterns (e.g., including wavelength, intensity, spatial information, etc. for each excitation signal emission system), wherein each light array pattern encodes a content frame. The frame rate of the timeseries can be between 50 FPS-500 FPS (e.g., greater than 50 FPS, greater than 80 FPS, 90 FPS, etc.), but can alternatively be less than 50 FPS or greater than 500 FPS. A pulse duration the excitation signal (e.g., defining the frame rate when the display includes a passive array of µLEDs) can be between 0.1 ms-100 ms (e.g., 1 ms-5 ms), but can alternatively be less than 0.1 ms or greater than looms. In a specific example, the emission parameters can include state change instructions for the excitation signal emission systems (e.g., when the display 100 includes an array of µLEDs driven by an active driver at the display 100). In variants, one or more emission parameters can be fixed (e.g., a fixed wavelength, fixed intensity, etc.) or variable.

The control instructions ("controls") for implant control (e.g., including the emission parameters) can be determined and/or adjusted by the external device 400, by the controller 300, the display 100, a combination thereof, and/or any other system component. In a first example, the controls can be determined at a processing system of the external device 400 based on: content (e.g., received from the sensor 450), cell state information (e.g., measured at the display 100 and transmitted to the external device 400 via a communication element of the controller 300), display information (e.g., current µLED states), controller state information (e.g., measured by a controller sensor), and/or any other information. In a second example, the controls can be determined at a processing system of the controller 300 based on: content (e.g., unprocessed and/or processed content received from the external device 400), cell state information (e.g., measured at the display 100 and transmitted to the controller 300 via the display-controller connector), display information, controller state information, and/or any other information. In a third example, the controls can be determined at a processing system of the external device 400 and a processing system of the controller 300 (e.g., adjusted by the controller 300).

The emission parameters are preferably determined based on content (e.g., visual data, sensory data, other external information, artificial data, any other data, etc.), but can additionally or alternatively be determined based on cell state, display information (e.g., the current state of each excitation signal emission system, wherein the emission parameters include a state change for all or a portion of the excitation signal emission systems), controller state information, calibration information, and/or any other information. For example, the emission parameters can be determined such that the resulting excitation signals collectively encode the content (e.g., the emission parameters prescribe a timeseries of light array patterns, wherein each light array pattern encodes a content frame). In a specific example, the emission parameters can be determined and/or adjusted such that the display 100 emits signals corresponding to an image (e.g., such that signals relayed to the brain based on the excitation signals can be interpreted by the brain as the image); in this example, the content can be a video and the image can be a frame of the video. In an illustrative example, the intensity of light emitted by each display unit can be controlled such that the display collectively projects a grayscale (e.g., single-channel) or color (e.g., multi-channel) version of the image.

The emission parameters can optionally be adjusted based on a retinal coding scheme (e.g., a mapping of classifications of retinal ganglion cell types in the retina), emission intensity calibration, manual feedback, and/or other calibration information. In a first embodiment, the emission parameters can be adjusted based on a cell state (e.g., measured by one or more signal sensor systems). In a first example, signal intensity is decreased when proteins (e.g., cell receptors) are deemed saturated. In a second example, signal intensity is increased when proteins are not activated in response to the signal emission. In a third example, the display 100 can include signal sensor systems (e.g., optical and/or electrical sensors) which can be used to determine a retinal coding scheme (e.g., based on an in vivo mapping of cell responses) which can be used to calibrate the emission parameters. In a second embodiment, the emission parameters can be manually adjusted. For example, feedback from a user (e.g., patient reports of the perceptual consequences of stimulation) can be used to determine a retinal coding scheme used to adjust the emission parameters. In an illustrative example, since cones often impinge on a single midget ganglion cell and humans can detect single cone simulation, users can consciously perceive single retinal ganglion cell (RGC) stimulation and report on the location and effect of the sensation.

However, the emission parameters can be otherwise determined.

Optionally, the display 100 can include one or more signal sensor systems (e.g., a light sensor system including an imaging sensor with recording electrodes and detector circuitry; a voltage sensor; current sensor; etc.). The signal sensor system functions to detect cell state information. The signal sensor system can measure: the presence and/or concentration of one or more cellular molecules (e.g., calcium ions), protein (e.g., cell receptor) response to an excitation signal (e.g., fluorescence spatial distribution, intensity, decay, etc.), protein response to a secondary signal (e.g., a different wavelength of light, a signal from another cell, etc.), protein mechanical response, and/or any other cell state metric. In a first variant, the signal sensor system can be associated with an excitation signal emission system. For example, the excitation signal emission system emits a first signal (e.g., a first wavelength of light emitted from the display 100 and received by the cell) that stimulates an optogenetic sensor in the cell to emit a second signal (e.g., a second wavelength of light emitted by the cell and received by the display 100), wherein the second signal is detected by the signal sensor system. In a specific example, the intensity of the second signal indicates the intensity of a cellular event (e.g., an activation potential firing from the cell), wherein the cellular event is caused by an optogenetic actuator receiving an initial signal emitted by an excitation signal emission system. In examples, the optogenetic sensor can be a different protein from the optogenetic actuator, wherein a single cell can include both the optogenetic sensor and optogenetic actuator, or only include one of the above. In a second variant, the signal sensor system can receive electrical signals (e.g., bioelectrical potential, electrical currents, changes thereof, etc.). The electrical signals can be emitted by the same cell associated with the excitation signal emission system, by a different cell, and/or any other biological and/or electrical component. For example, a feedthrough can be used to connect electrical sensors (e.g., voltage and/or current sensors) in the signal sensor system to the cell(s). In an illustrative example, the electrical sensor is inserted (e.g., via a prong, spike, other projection, etc.) into the retina surface (e.g., 10 μm-200 μm, 50 μm, 100 μm, any range or value therebetween, less than 10 μm, greater than 200 μm, etc.). In specific examples, directly recording electrical signals from cells can reduce crosstalk (e.g., optical signals from the excitation signal emission system minimally excite the electrical sensors in the signal sensor system), which can be particularly important in low signal-to-noise ratio conditions such as neural recording.

In a first example, the signal sensor systems can be used for calibration. In a specific example, the signal sensor systems can ensure the intensity of light emitted by the light emission systems is calibrated to be above an activation threshold (e.g., an activation threshold of a cell protein) and/or below a saturation threshold. In a second example, the signal sensor systems can be used to determine cell activity, wherein stimulation by the excitation signal emission system can optionally be conditioned based on the cell activity. In a specific example, the emission parameters can be dependent on the cell activity when the display 100 is used directly in the brain and cells in the display-brain interface 200 are receiving additional signals from neurons. Optionally, the display 100 can transmit cell state information to: the controller 300 (e.g., to calibrate emission parameters), display processing circuitry (e.g., to directly calibrate light emission systems), an external device 400, and/or any other system.

In an illustrative example, one display unit includes: a first signal element with a light emission system that emits a first wavelength of light configured to stimulate a first cell having an optogenetic actuator (e.g., for neuron signaling; by activating the optogenetic actuator of the first cell); a second signal element with a light emission system that emits a second wavelength of light configured to stimulate a second cell having an optogenetic sensor (e.g., wherein the second wavelength of light stimulates the optogenetic sensor to emit light at a third wavelength based on the cell state); and a third signal element with a light sensor system that detects light at the third wavelength from the second cell. In this example, the first cell can be the second cell (e.g., wherein a single cell has an optogenetic actuator and an optogenetic sensor) or the first cell can be distinct from the second cell (e.g., wherein the first cell is associated with the first signal element and the second cell is associated with the second and third signal elements).

Figure 23A:
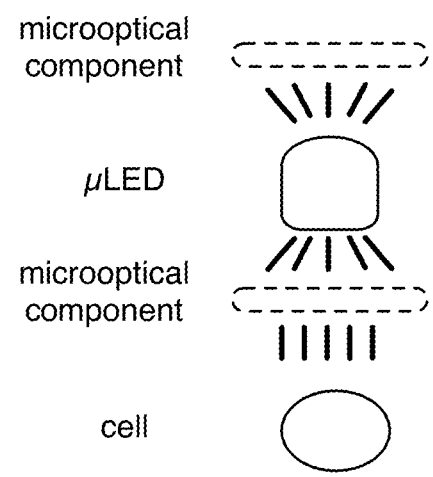
FIGS. 23A and 23B depict examples of optics components.
Figure 23B:
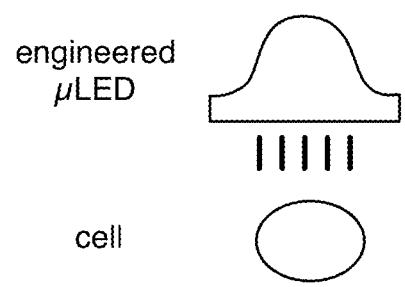

The display 100 can optionally include and/or be coupled (e.g., adhered, mounted, etc.) to one or more optics components (e.g., microoptical components). The optics component can function to collimate light, homogenize light, focus light (e.g., onto a smaller number of cells), reduce light shining back through the eye lens, and/or otherwise modify light emitting to or from the display 100. The optics component can be located on the front of the display 100 (facing the display-brain interface 200) and/or back of the display 100; an example is shown in FIG. 23A. In a first variant, the optics component includes a lens (e.g., microlens, diffractive lens, metalens, etc.). In a specific example, the lens can be positioned in front of each μLED (e.g., on the emitting side) to collimate the light from the μLED towards one or more cells in the display-brain interface 200. In a second variant, the optics component includes a back reflector (e.g., located on the back of the display 100, located on the backside of each μLED, etc.). In examples, the back reflector can be a metal (e.g., aluminum, silver, etc.), a Bragg reflector, and/or any other reflector. In a third variant, the optics component can include an engineered PLED, wherein the engineered μLED is the μLED of an excitation signal emission system. An example is shown in FIG. 23B. In a first example, the engineered PLED has a smaller emitter, which can have an improved emission profile (e.g., including collimated light). In a first specific example, the entire μLED can be engineered to be smaller. In a second specific example, a pumped area of the quantum well of the μLED can be engineered to be smaller. In a second example, the μLED can have a modified shape. In a specific example, the μLED can have a parabolic shape on the backside of the PLED (e.g., creating a parabolic back reflector). In a third example, an optics component can be coupled to the μLED (on the emitting side and/or the front side). In a fourth example, the PLED can include a buffer layer (e.g., gallium nitride) on the emitting side, which can be patterned to function as an optics component. In a fourth variant, the optics component can be a combination of the first, second, and/or third variants. The mapping between optics components and light emission systems can be: 1:1 (e.g., one optics component for each μLED), 2:1, 1 optics component for the entire set of display units (e.g., a back reflector spanning the display 100), and/or any ratio between optics components and signal elements.

However, the display 100 can be otherwise configured.

The system can optionally include a display-controller connector, which can function to connect the display 100 to the controller 300. The display-controller connector preferably includes electronic connections (e.g., wires, metal lines, traces, etc.) that physically connect the display 100 to the controller 300, but can alternatively include a wireless connection (e.g., Bluetooth, BLE, NFC, IR, RF, etc.). The number of connections on the display-controller connector can be between 1-10,000 or any range or value therebetween (e.g., 5-1000, 5-20, 100-1000, 10-500, greater than 100, greater than 200, greater than 500, greater than 1000, etc.), but can alternatively be greater than 10,000. Each connection can be between 0.5 μm-100 μm or any range or value therebetween (e.g., 2 μm-10 μm, 5 μm, etc.), but can alternatively be less than 0.5 μm or greater than 100 μm. The display-controller connector can include a single row of connections, multiple rows of connections (e.g., stacked), and/or any other configuration of one or more connections. The connections can be adhered to a backing, encapsulated within an encapsulant, and/or otherwise supported. The thickness of the display-controller connector can be between 5-150 μm or any range or value therebetween (e.g., 10 μm-30 μm, less than 30 μm, less than 20 μm, etc.), but can alternatively be less than 5 μm or greater than 150 μm. The width of the display-controller connector can be between 0.5 mm-100 mm or any range or value therebetween (e.g., 1 mm-5 mm, 2 mm, less than 50 mm, less than 20 mm, less than 10 mm, less than 5 mm, etc.), but can alternatively be less than 0.5 mm or greater than 100 mm. The length of the display-controller connector (e.g., the length of each connection) can be between 1 mm-1 cm or any range or value therebetween (e.g., 5 mm-100 mm, 10 mm-40 mm, etc.), but can alternatively be less than 1 mm or greater than 1 cm. The display 100 and the display-controller connector can be fabricated on the same wafer, be assembled together after display 100 fabrication, and/or be otherwise manufactured.

In a first example, the display 100 includes an active driver (e.g., with logic components located at the display 100). In this example, the display-controller connector can optionally include fewer wires than the number of pixels. In a second example, the display 100 includes a passive driver. In this example, the display-controller connector can include a plurality of wires (e.g., one for each pixel or set thereof; one for each pixel-color channel combination, etc.); alternatively, the display-controller connector can include less wires (e.g., with lower cardinality relative to the display units).

However, the display-controller connection can be otherwise configured.

The system can optionally include a display-brain interface 200, which functions to convert the excitation signals from the display 100 to neural signals interpretable by the brain.

Figure 30:
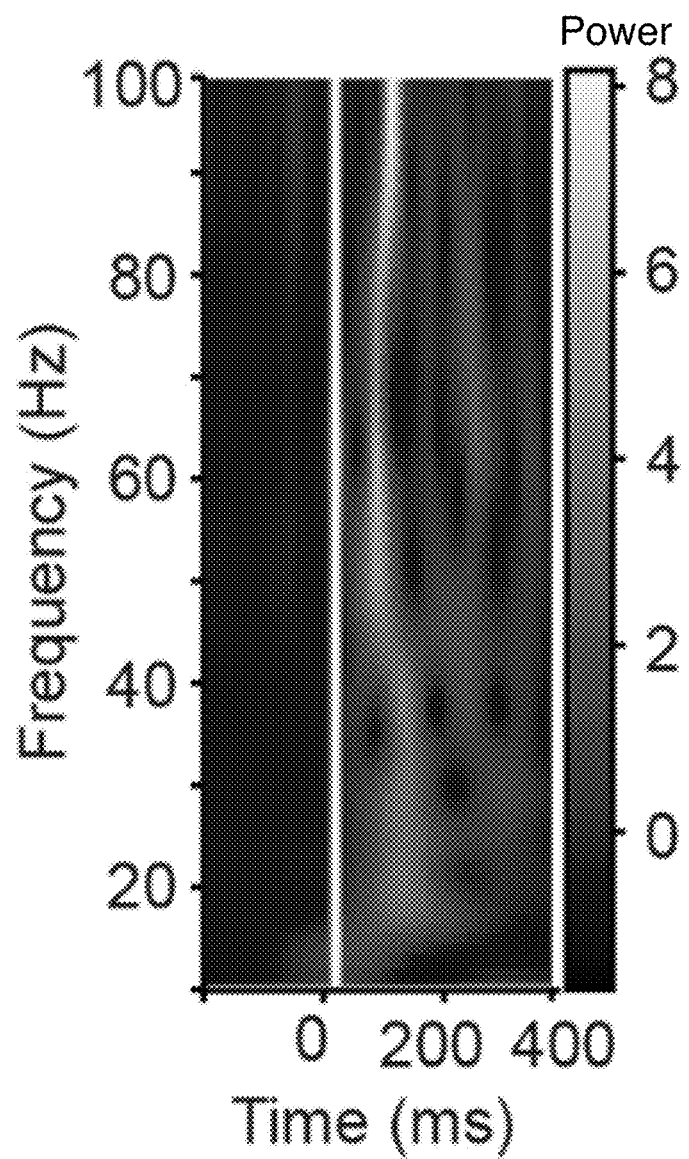
FIG. 30 depicts an example spectrogram showing the power as a function of frequency over time after presentation of an optogenetic stimulus through an example retinal implant system; measured using an implanted electrocorticography grid.
Figure 31A:
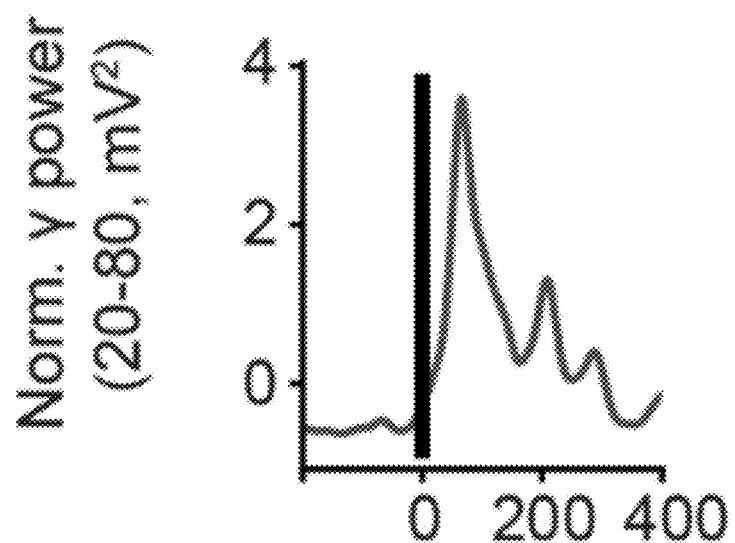
FIG. 31A depicts an example of normalized gamma power versus time resulting from stimulus presentation from an example retinal implant system; measured using an implanted electrocorticography grid.
Figure 31B:
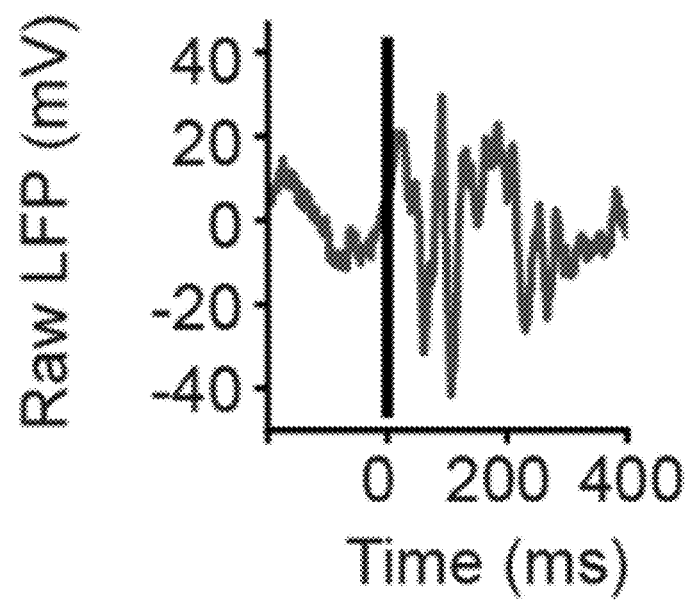
FIG. 31B depicts an example of raw local field potential (LFP) versus time-resulting from stimulus presentation from an example retinal implant system; measured using an implanted electrocorticography grid.
Figure 32:
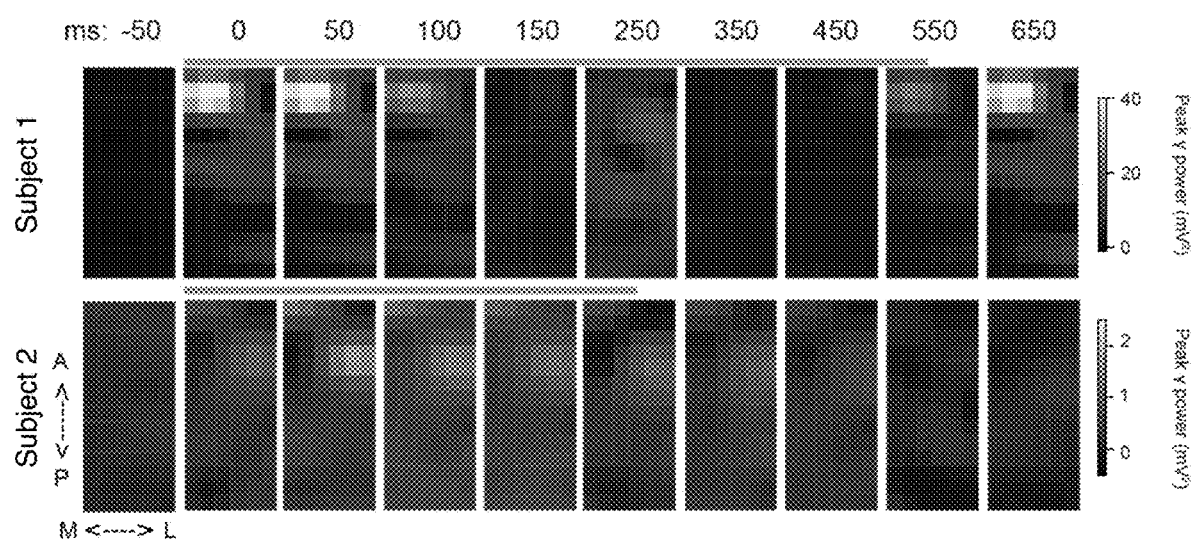
FIG. 32 depicts an example series of heatmaps measured using an implanted electrocorticography grid, showing peak gamma power (20-80 Hz, mV2) as a function of time from an example retinal implant system stimulus onset (top, green bar), versus position on the grid (M-L: medial, lateral; A-P: anterior, posterior).
Figure 33:
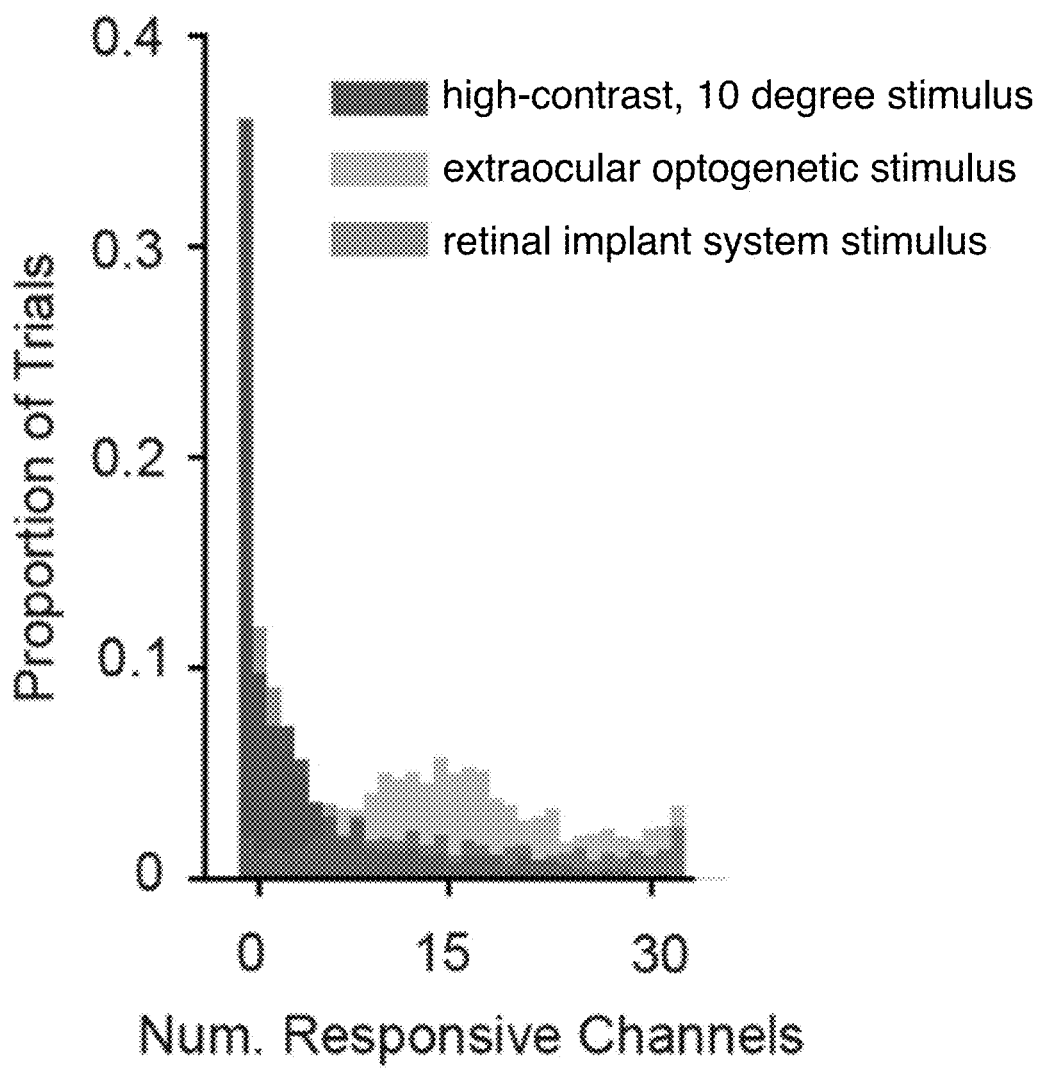
FIG. 33 depicts an example histogram showing the number of significantly responding electrocorticography channels (implanted electrocorticography grid; max 32 responding channels) for each trial of optogenetic stimulation using an example retinal implant system compared to extraocular optogenetic stimulus and high-contrast 10 degree visual stimulus.

The display-brain interface 200 preferably includes a set of cells that are connected (e.g., directly or indirectly) to the brain, but can be otherwise configured. The display-brain interface 200 is preferably located in the signaling pathway between the display 100 and the nervous system (e.g., brain), but can be otherwise arranged. In a specific example, the cells, when activated by excitation signals from the display 100, can evoke activity in the visual cortex (e.g., evoke a focal visual-evoked potentials in the visual cortex). Examples are shown in FIG. 30, FIG. 31A, and FIG. 31B. In an illustrative example, a display 100 corresponding to ~10 degrees of visual space in humans (e.g., with an active area of 2.56×2.56 mm) can stimulate patterns of evoked activity resembling visual-evoked potentials elicited by high-contrast 10 degree stimuli much more than those from full-field optogenetic stimulation from outside the eye (e.g., examples shown in FIG. 32 and FIG. 33).

In a first variant, the display-brain interface 200 includes native, unmodified cells. For example, the display-brain interface 200 can include photoreceptors (e.g., wherein the display 100 emits light that is detected by the photoreceptors), plexiform layer cells, retinal ganglion cells, neurons, and/or any other cell that directly or indirectly interfaces with the nervous system.

In a second variant, the display-brain interface 200 includes, creates, and/or leverages genetically modified cells. Genetically modified cells can include optogenetically modified cells with light-sensitive biochemical signaling pathways (e.g., such that the cells produce biochemical signals in response to detecting certain wavelengths of light), hypoimmune cells (e.g., genetically modified to reduce immune response due to display 100 implantation), genetically modified to include a small molecule killswitch (e.g., transfected with a killswitch gene), a combination thereof, and/or other genetically modified cells. Examples of cells that can be genetically modified include: organoids (e.g., with multiple retinal cell types), cells selected from an organoid (e.g., a specific cell type), retinal ganglion cells, plexiform layer cells (e.g., wherein the plexiform layer cells can signal to native retinal ganglion cells), photoreceptors, any cells used in vision, neurons, stem cells (e.g., wherein the stem cells are genetically modified prior to differentiation), any animal cell (e.g., human cell), and/or any other cell. In specific examples, the cells can include neurons, retinal ganglion cells, and/or other cells derived from pluripotent stem cells. The cells can be native to the display 100 implant location (e.g., modified in situ) and/or developed outside the implant location (e.g., modified and/or grown in vitro; user stem cells extracted and optionally differentiated; etc.).

In variants leveraging modified cells, the cells can be genetically modified by transfecting cells with a light-sensitive protein (e.g., using a virus with a plasmid and capsid) that acts as an optogenetic actuator (e.g., optogenetic effector) and/or optogenetic sensor. Optogenetic actuators produce a biochemical signal (e.g., an action potential) in response to receiving light at a specific wavelength; optogenetic sensors produce light at a specific wavelength based on (e.g., proportional to) a state of the cell (e.g., a concentration of a given molecule). However, optogenetic actuators and optogenetic sensors can be otherwise defined. In variants, optogenetic sensors can be coupled to optogenetic actuators in a cell (e.g., a fusion construct) such that when the optogenetic actuator receives a first wavelength of light the optogenetic sensor is activated to can emit a second wavelength of light based on the cell state.

In examples, the cells (e.g., native retinal ganglion cells) can be transfected using: an intravitreal injection, periretinal injection, sub-internal limiting membrane injection (e.g., guided by optical coherence tomography), injection post-vitrectomy and post-internal limiting membrane peel, injection through holes in the internal limiting membrane created using an NdYAG laser, and/or any other transfection method. The cells can be transfected in situ (e.g., in the eye), ex situ (e.g., outside of the eye and subsequently implanted into the eye), and/or in any other suitable location. The virus used to transfect the cells can optionally be targeted to a specific cell type (e.g., general soma cells, neurons, retinal ganglion cells, a type of retinal ganglion cell, stem cells, etc.). The capsid can be an adeno-associated virus capsid (e.g., AAV2.7M8) and/or any other suitable capsid. The plasmid can be an opsin, a fluorescent biosensor protein, and/or any other suitable plasmid. Opsin examples include: CheRiff, ChroMD, ChroME, ChroME2S, ChRmine (e.g., ChRmine-mScarlet), ChrimsonR (e.g., including red-shifted variants), ReachR, and/or any other opsin. In an illustrative example, the cells can be transfected using: AAV2.7m8 hSyni-ChRmine-Kv2.1-WPRE. Fluorescent biosensor protein examples include: GCaMP8s, GCaMP8m, jRGecoia, YCaMP, iGECI, and/or any other suitable protein. The opsin can be activated by blue light, green light, red light, and/or any other wavelength. Different plasmids (e.g., with different wavelength sensitivities) can optionally be used for content transfer (e.g., input), sensing, (e.g., cell monitoring), and/or sensing activation. Different plasmids can optionally be used for different types of content (e.g., different communication modalities). Different plasmids can optionally be used for different types of cells (e.g., different types of ganglion cells), wherein the wavelengths of light emitted by the excitation signal emission systems are tailored to the cell type. However, any optogenetic method can be implemented.

In variants, the number of opsin-expressing cells can be reduced. In a first example, cell-type specific expression can be encoded via a promoter. In a first specific example, the promoter can be a CAG promoter, which can express opsin in most infected cells. In a second specific example, the promotor can be human synapsin promoter, which can confine opsin expression to neuronal cells. In a second example, the virus can be spatially restricted (e.g., spatially restricted within the retina). In an illustrative example, the virus can be embedded on the display surface (e.g., with a silk fibroin hydrogel), which can significantly decrease the number of opsin-expressing cells in the eye without changing the function of the device.

The cells (e.g., unmodified or modified cells) are preferably located such that they can transmit and/or receive signals to and/or from the display signal elements, but can additionally or alternatively be located separate from the display signal elements. In variants, the modified cells can be sparse (e.g., separated by a minimum distance, such as 1 ⌈m, 5 ⌈m, 10 ⌈m, or more), dense (e.g., separated by no more than a threshold distance), and/or otherwise arranged.

Figure 13A:
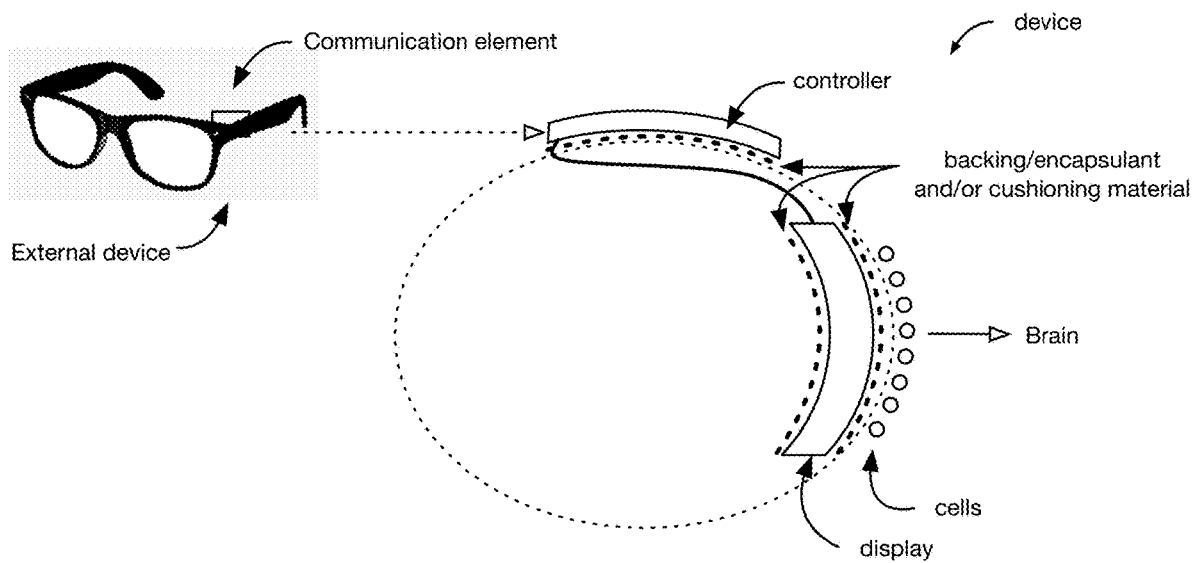
FIG. 13A depicts an illustrative example of the system, not including a cell support.
Figure 13B:
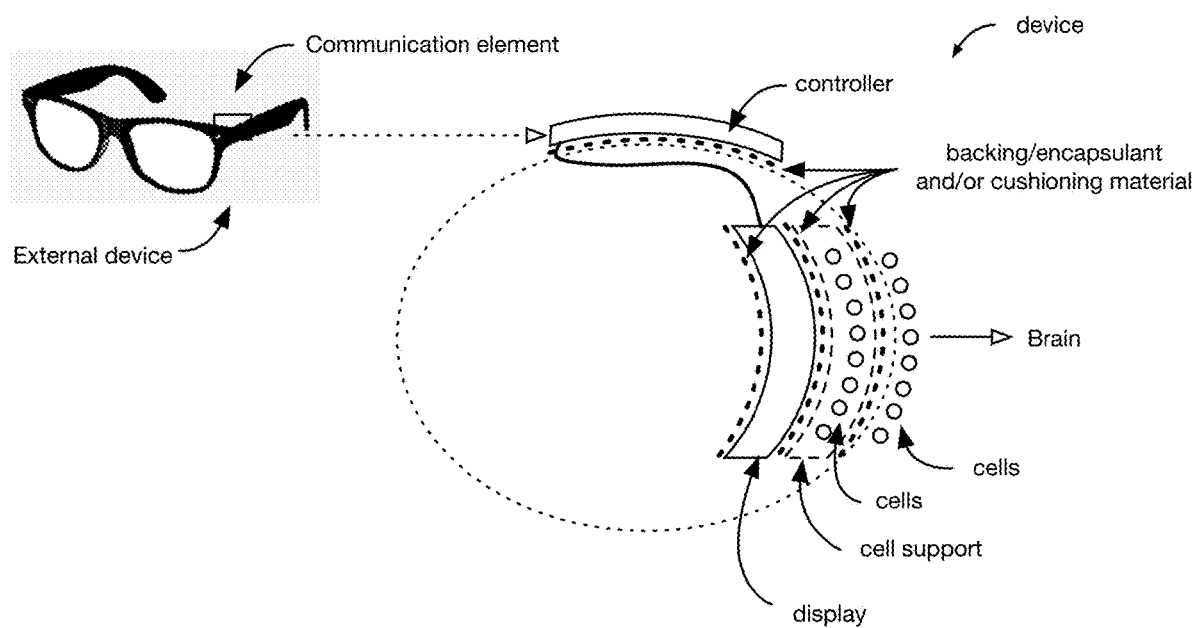
FIG. 13B depicts an illustrative example of the system, including a cell support.

In a first variant, the cells are located in a cell support that is connected to (e.g., adhered to) and/or a part of the display 100 (e.g., wherein the cells can be genetically modified before they are seeded into the cell support and/or after seeding into the cell support). An example is shown in FIG. 13B. In examples, the cell support can be adhered to the display 100 using adhesives (e.g., epoxy), polymerization, and/or any other suitable methods. The cell support is preferably adhered to the display 100 with a gap between the cell support and the display 100 (e.g., to improve optics), but can alternatively be adhered directly to the display 100. The gap can be between 10 nm-20 μm or any range or value therebetween, but can alternatively be less than 10 nm or greater than 200 μm. Preferably, the body of the cells are trapped by the cell support while the cell projects axons and/or dendrites out of the cell support to interface with native cells. Alternatively, the cell can be completely trapped (e.g., with no axon or dendrite projection) or not trapped (e.g., the cell body can move outside the cell support). Examples of methods to trap cells include: swelling hydrogels, a capping layer adhered to the cell support after seeding (e.g., closing cell support microwells), chemical functionalization of faces of the cell support (e.g., via surface treatments) that can promote cell growth and/or inhibit cell growth, and/or any other trapping methods.

Figure 12:
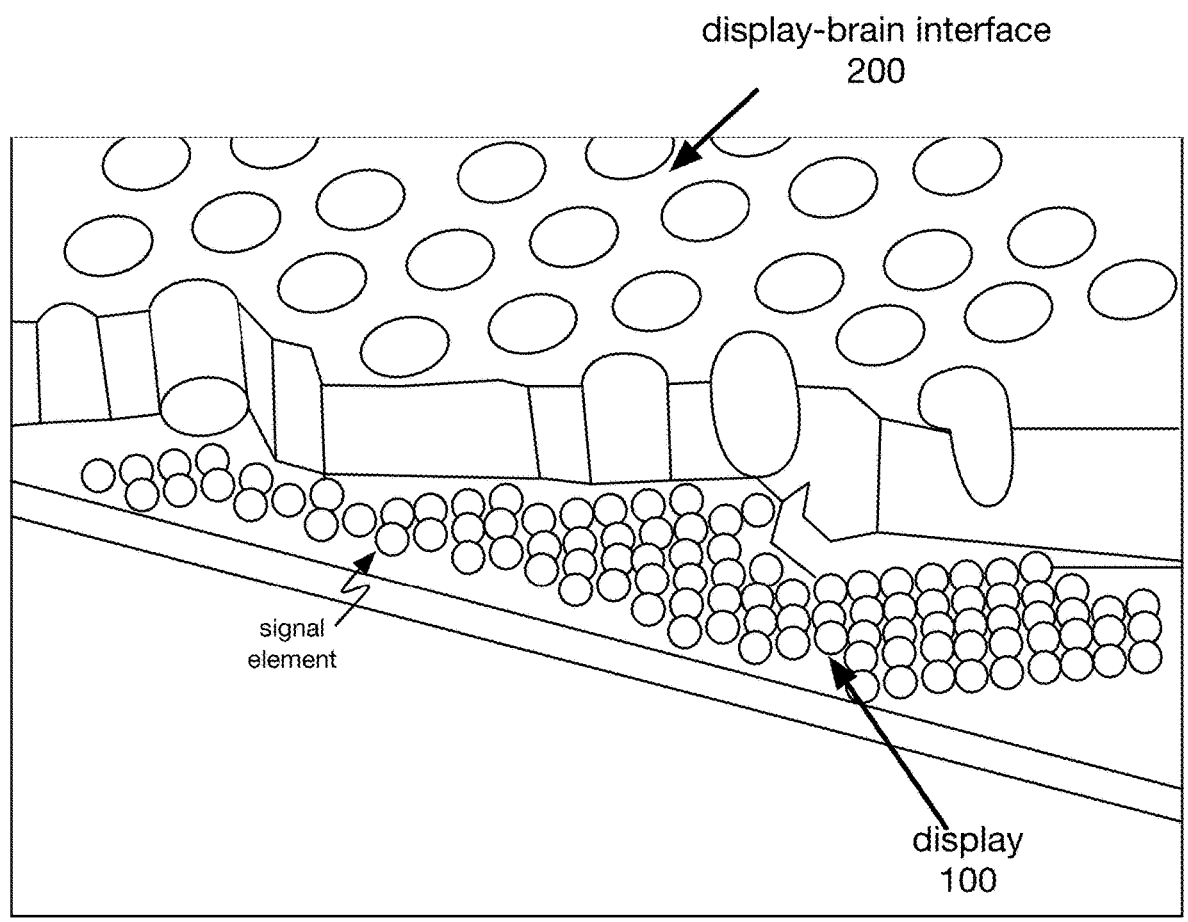
FIG. 12 depicts an illustrative example of a display and a display-brain interface.

In a first example, the cell support is a matrix defining a set of cell retention units (e.g., microwells; examples shown in FIG. 12 and FIG. 14) configured to retain one or more cells. Cell retention units can be open, closed, and/or have any other geometry. The matrix material can be a flexible polymer, a substantially rigid material, and/or any other suitable material. The pattern of cell retention units and/or cell pattern (e.g., the separation between cells, the frequency of cells, etc.) is preferably equivalent to or based on the display unit pattern (e.g., each signal element corresponds to a cell), but can alternatively be any other pattern. In an illustrative example, each display unit and/or signal element thereof (e.g., each μLED) corresponds to a single cell retention unit, wherein the single cell retention unit is configured to retain a single cell. Examples are shown in FIG. 4A, FIG. 4B, FIG. 4C, FIG. 4D, FIG. 4E, and FIG. 4F. In a second example, the cell support is a gel (e.g., a hydrogel). However, any other suitable cell support can be used.

In a first embodiment, the cells in the cell support function as photoreceptors (e.g., the cells interface with retinal ganglion cells, optionally replacing nonfunctional photoreceptors). In a second embodiment, the cells function as retinal ganglion cells (e.g., the cells interface with neurons in the brain). In a third embodiment, the cells function as neurons (e.g., located in the brain, directly interfacing with other neurons). However, the cells can otherwise function to interface with the nervous system.

Figure 5A:
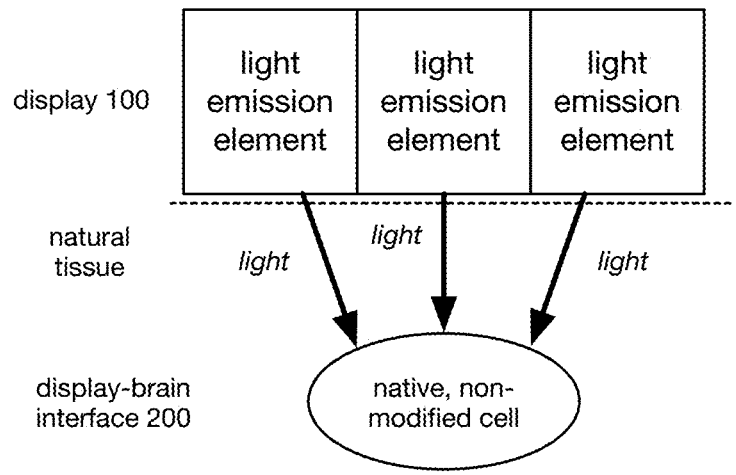
FIG. 5A depicts an example of the system, wherein the display-brain interface includes native, non-modified cells.
Figure 5B:
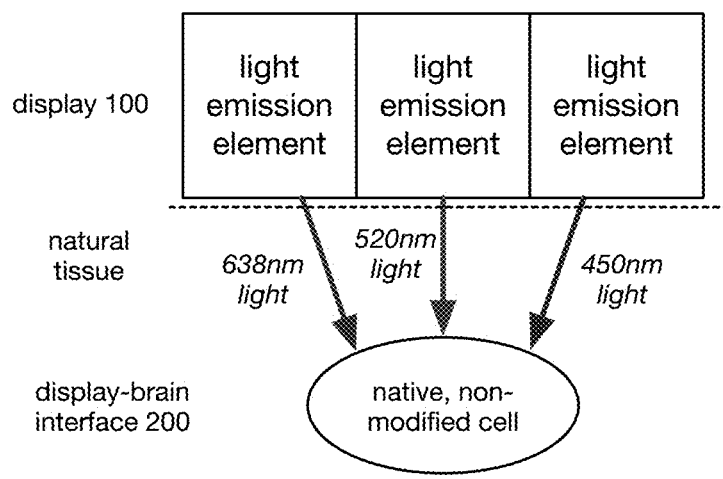
FIG. 5B depicts an illustrative example of the system, wherein the display-brain interface includes native, non-modified cells.

In a second variant, the cells are located in their native location (e.g., retinal ganglion cells, neurons in the visual cortex, cells in the brain stem, etc.). In a first example, the native cells are genetically modified in situ (e.g., converting the native, unmodified cells to genetically modified cells); examples are shown in FIG. 3A, FIG. 3B, FIG. 3C, FIG. 3D, FIG. 3E, and FIG. 3F. In a second example, the native cells remain unmodified; examples are shown in FIGURE SA and FIG. 5B. However, the cells can be located in any location and/or in multiple locations.

However, the display-brain interface 200 can be otherwise configured.

The controller 300 functions to communicate with an external device 400 and to control system operation (e.g., display 100 operation) based on the communication (e.g., based on emission parameters determined based on the communication and/or received via the communication). The controller 300 can optionally function to power the display 100, wherein the controller 300 itself can be powered by an external power source or an onboard power source (e.g., battery). The controller 300 is preferably not physically connected to the external device 400, but can alternatively be physically connected. The controller 300 is preferably physically connected to the display 100 (e.g., via physical wires in the display-controller connector), but can alternatively be not physically connected to the display 100 (e.g., wherein emission parameters are transmitted to the display 100 wirelessly). The controller can optionally be coupled to multiple displays (e.g., to increase the total display surface area without increasing implantation incisions). The power source 500 and/or components thereof can optionally be within the controller 300, coupled to the controller 300 (e.g., outside the controller volume), and/or otherwise connected to the controller.

Figure 18A:
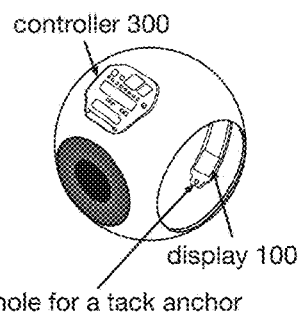
FIG. 18A depicts a third illustrative example of the system.
Figure 18B:
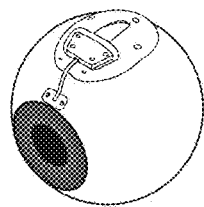
FIG. 18B depicts an illustrative example of an Ahmed valve.
Figure 18C:
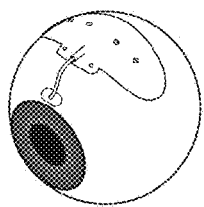
FIG. 18C depicts an illustrative example of a Baerveldt shunt.
Figure 19A:
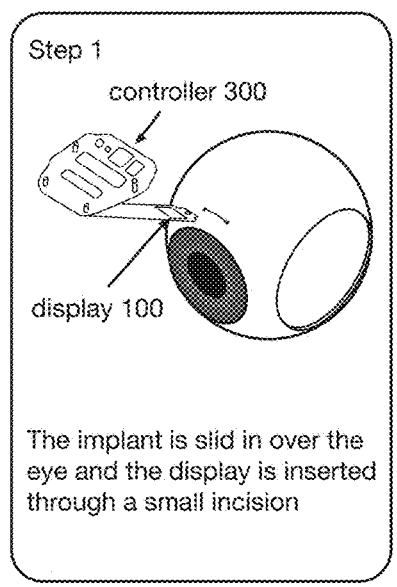
FIGS. 19A-19C depict example steps of implanting a display and a controller.
Figure 19B:
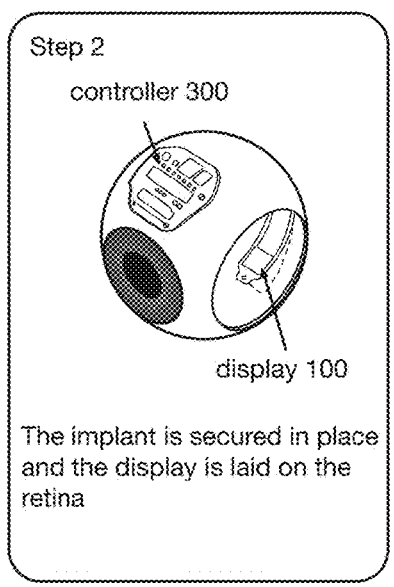
Figure 19C:
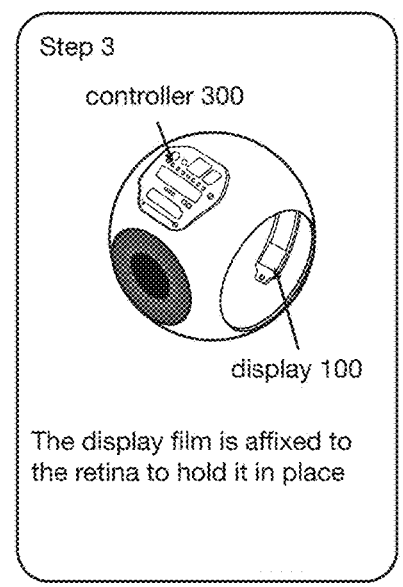

The controller 300 is preferably flexible, but can alternatively be rigid and/or have both flexible and rigid components. The controller thickness can be between 0.1 mm-20 mm or any range or value therebetween (e.g., 0.5 mm-2 mm, less than 10 mm, less than 5 mm, less than 2 mm, etc.), but can alternatively be less than 0.1 mm or greater than 20 mm. The controller 300 volume can be between 50 μL-500 μL or any range or value therebetween (e.g., 100 μL-200 μL, 130 μL-150 μL, etc.), but can alternatively be less than 50 μL or greater than 500 μL. The controller 300 preferably fits within the footprint of a glaucoma tube shunt device (e.g., 50 mm$^2$-500 mm$^2$), but can alternatively be larger or smaller than the glaucoma tube shunt device (e.g., a conventional glaucoma drainage implant) footprint. In a specific example, the controller can have the form factor of the glaucoma tube shunt device. Examples are shown in FIGS. 18A-18C.

Figure 11:
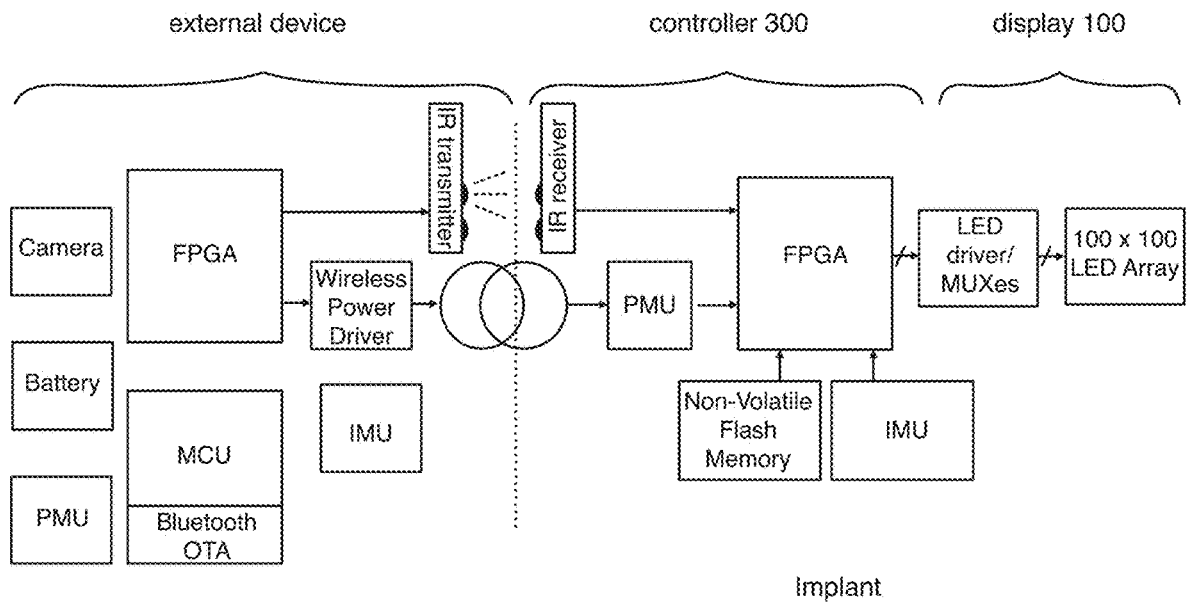
FIG. 11 is a schematic representation of an illustrative example of the system.

The controller 300 can optionally include one or more: communication elements, the power source 500 and/or components thereof (e.g., power receiver components, power rectification and/or regulation components, etc.), a processing system (e.g., processor, memory, data processing circuitry, etc.), filters, controller sensors, memory (e.g., flash memory to store instructions), analog-to-digital converter, additional safety features, and/or any other system component. In an example, the processing system includes an integrated circuit (e.g., field-programmable gate array (FPGA), microcontroller, system-on-a-chip, etc.). An example is shown in FIG. 11.

The controller sensors can function to measure a controller state, and can additionally or alternatively determine an implant state (e.g., including the controller state, a display state, etc.). The controller 300, external device 400, and/or display 100 can optionally be controlled based on the controller state. In a first example, power can be halted to one or more components in response to detection or occurrence of a predetermined controller state (e.g., indicating a water ingress, temperature above a threshold, etc.). In a second example, content and/or emission parameters therefrom can be adjusted based on the controller state (e.g., processing the content based on the pose and/or motion of the controller). The controller state can include: temperature, humidity, motion, pose (e.g., including position and/or orientation), electrical shorts (in the controller 300, in the display 100 connected to the controller 300, etc.) and/or any other information associated with the controller, wherein the controller can include one or more sensors that measure the respective parameter. In a first example, the controller 300 can include a motion sensor (e.g., inertial measurement unit, retroreflector, other optical components, etc.), which functions to track the position, orientation, and/or movement of the eye (e.g., the gaze of the eye) and/or one or more components of the system. The motion sensor preferably tracks motion with 3 DoF-6 DoF or any range or value therebetween, but can alternatively track motion is less than 3 DoF or greater than 6 DoF. In a second example, the controller 300 can include a temperature sensor, which functions to detect overheating. In a third example, the controller 300 can include a moisture sensor (e.g., a humidity sensor), which functions to detect ingress of water into the controller 300. In a fourth example, the controller 300 can include a current measurement sensor, which functions to detect a short (e.g., in the display 100).

Figure 2:
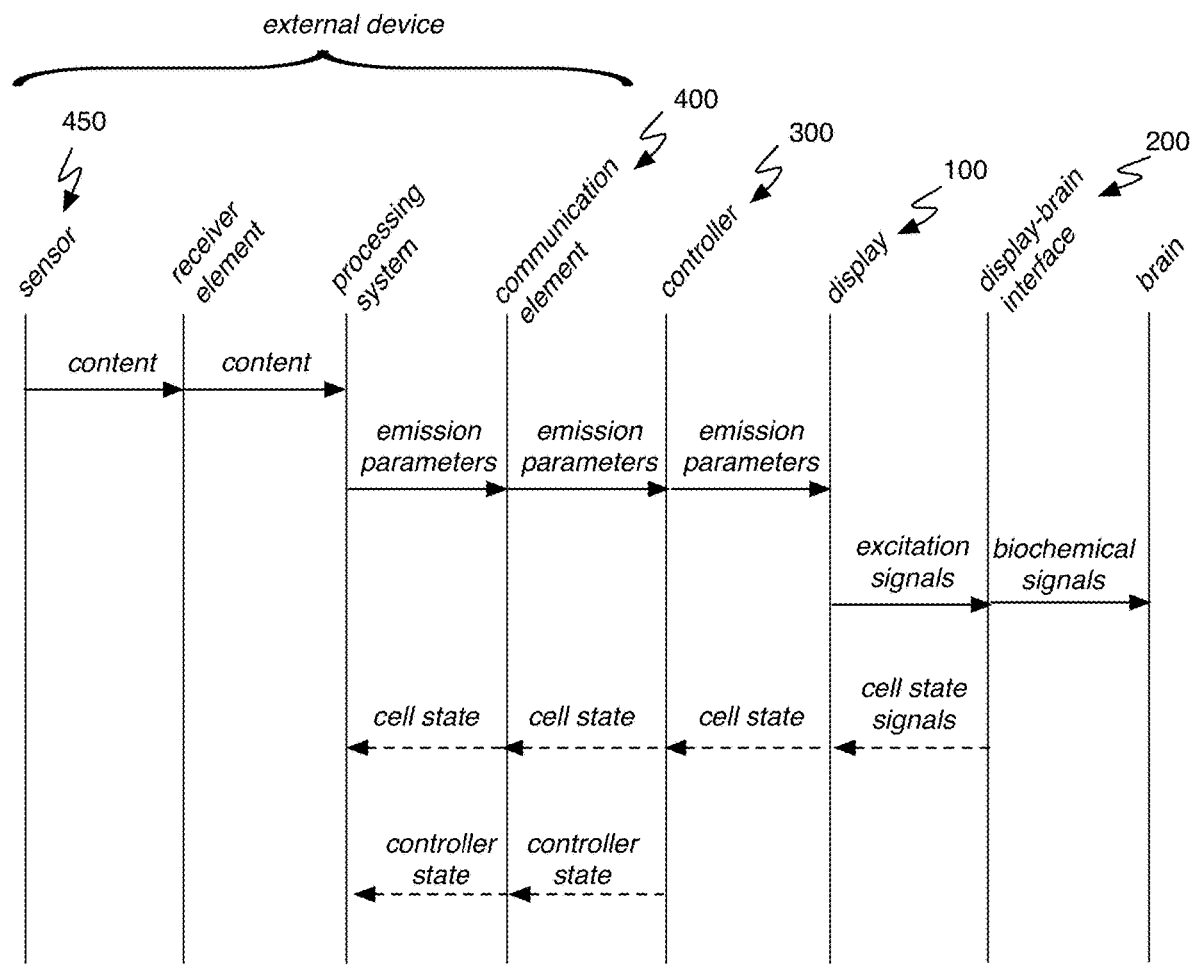
FIG. 2 is a schematic representation of an illustrative example of data transfer between components of the system.
Figure 3A:
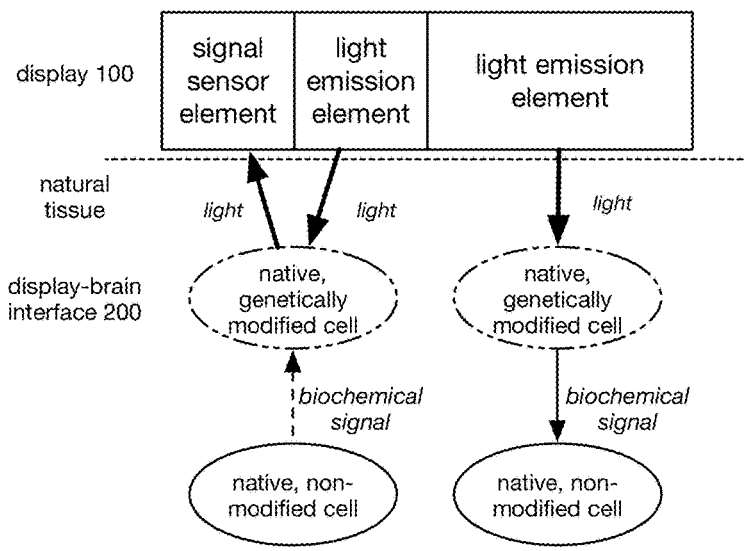
FIGS. 3A, 3B, and 3C depict examples of the system, wherein the display-brain interface includes native cells, genetically modified in situ.
Figure 3B:
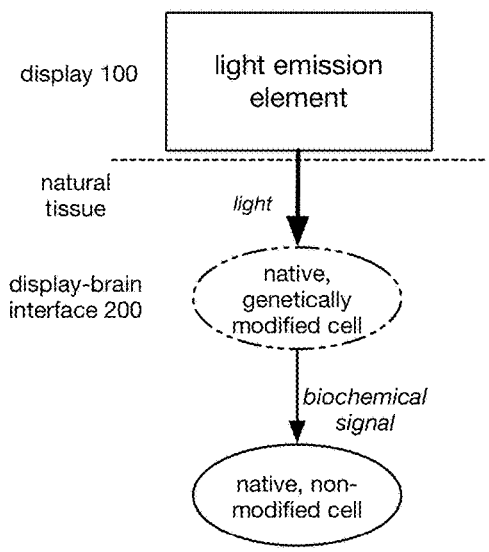
Figure 3C:
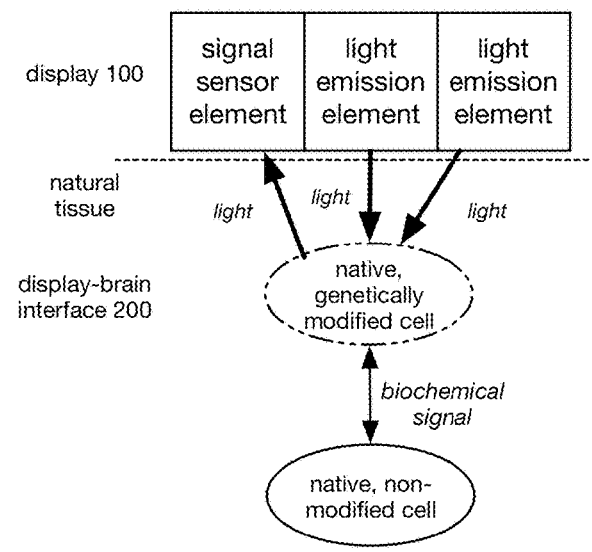
Figure 3D:
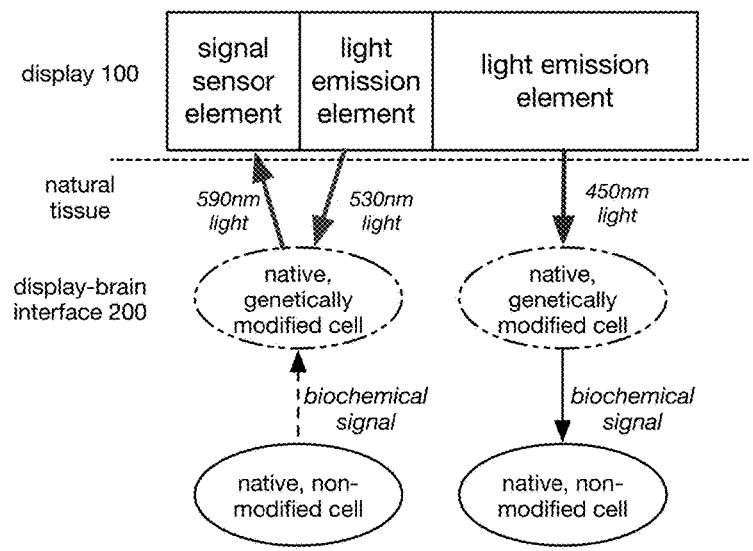
FIGS. 3D, 3E, and 3F depict illustrative examples of the system, wherein the display-brain interface includes native cells, genetically modified in situ.
Figure 3E:
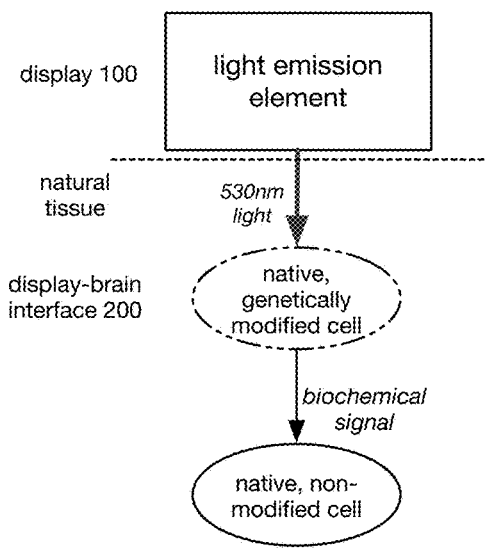
Figure 3F:
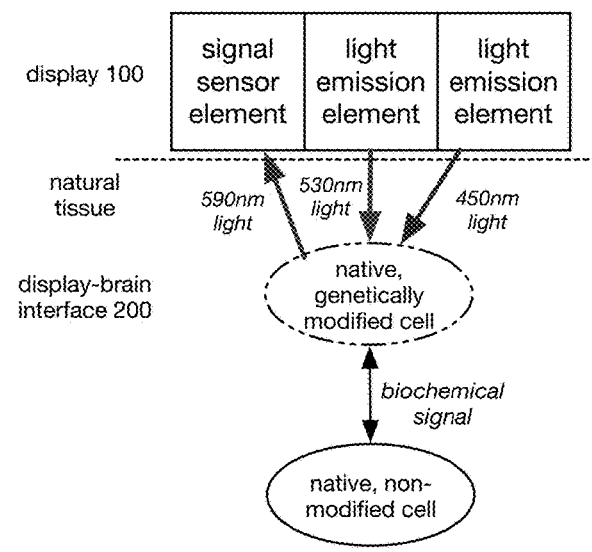
Figure 4A:
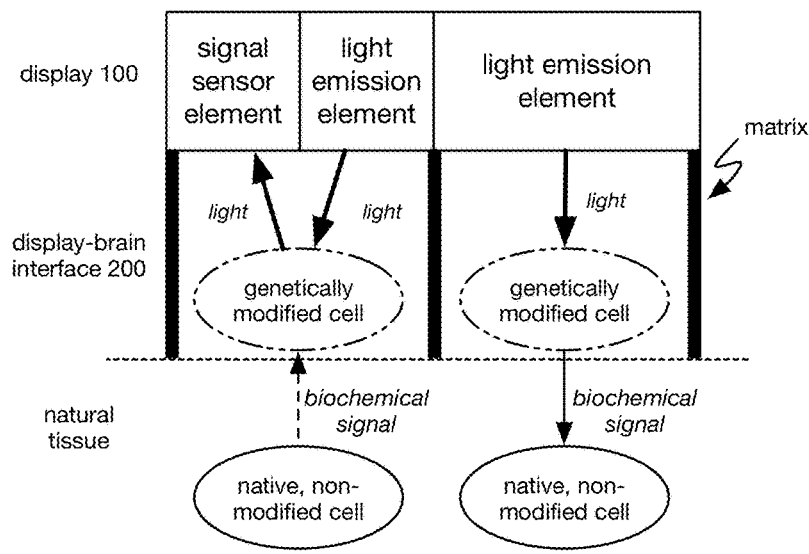
FIGS. 4A, 4B, and 4C depict examples of the system, wherein the display-brain interface includes genetically modified cells seeded in a cell support.
Figure 4B:
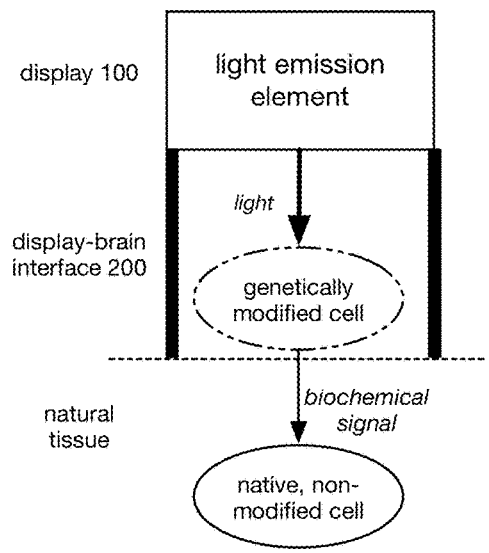
Figure 4C:
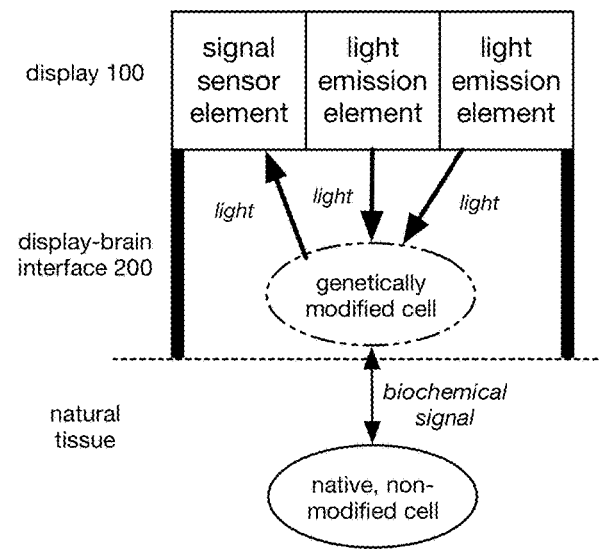
Figure 4D:
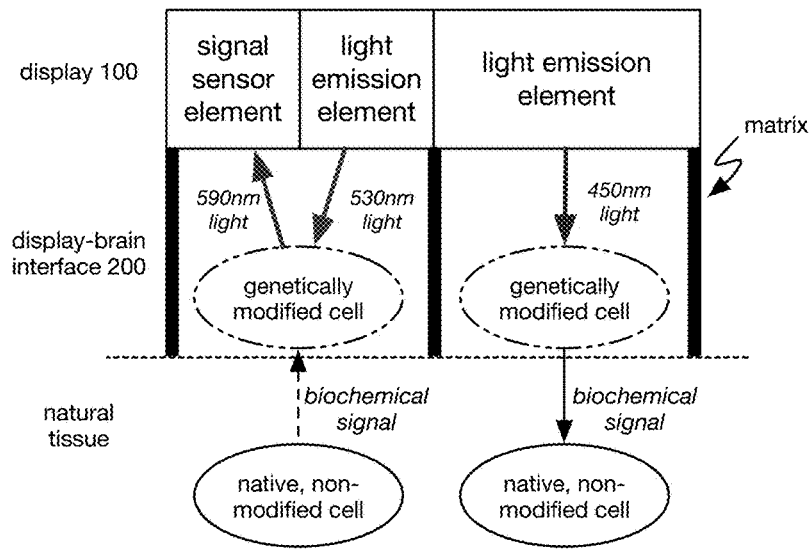
FIGS. 4D, 4E, and 4F depict illustrative examples of the system, wherein the display-brain interface includes genetically modified cells seeded in a cell support.
Figure 4E:
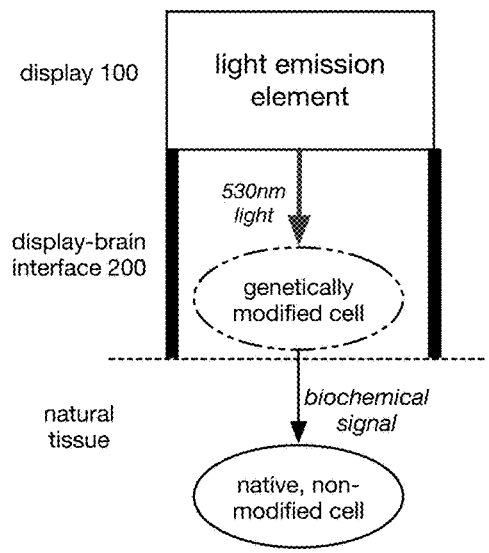
Figure 4F:
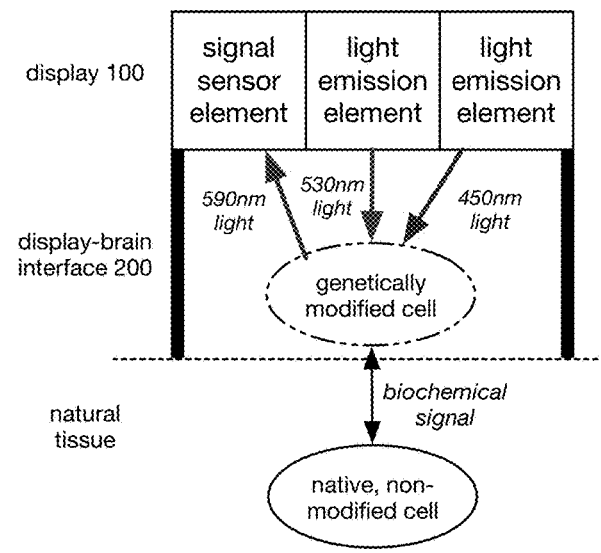

The communication element(s) of the controller 300 can include: receivers, transmitters, wired connections, and/or any other components. Controller communication with the display 100 can be through the display-controller connector and/or through any other connection. Controller communication with the external device(s) can be through: wireless communication (e.g., radio frequency (RF), infrared (IR), Bluetooth, BLE, NFC, another transmission frequency, the same or different wavelength as that used to stimulate the display-brain interface 200, etc.), wired communication, and/or any other connection. In a specific example, the controller includes IR diodes and an associated integrated circuit. Information received by the communication element of the controller 300 can include: content (e.g., wherein the controller calculates the emission parameters based on the received content), emission parameters (e.g., calculated by the external device 400), cell measurements (e.g., cell states measured by the display 100), and/or any other information. Information transmitted by the communication element of the controller 300 can include: emission parameters (e.g., transmitted to the display 100), controller measurements (e.g., controller states measured by the controller sensor), a controller pose signal (e.g., emitted light received by the tracking sensor of the external device 400), and/or any other information. Information transferred between the external device 400 and the controller 300, between the controller 300 and the display 100, and/or between any other system components can be transferred in real time (e.g., responsive to a request, responsive to a sensor 450 sampling a measurement, etc.), iteratively, asynchronously, periodically, and/or at any other suitable time. An illustrative example of information transfer is shown in FIG. 2.

The controller 300 can be: implanted, collocated with the display 100, located ex situ, and/or otherwise located. In examples, the controller can be located: on the eye, inside the eye, within the eye socket, on or near the brain (e.g., the brain surface, the brain stem, etc.), on or near the spine (e.g., the spinal cord), any subcutaneous location, on or near the ear (e.g. the ear canal), and/or any other location. In a first embodiment, the controller 300 is an extraocular component of the system, located on the globe of eye (e.g., with a similar form factor and/or location to a glaucoma tube shunt device). In this embodiment, the controller 300 is preferably located on the sclera, under the conjunctiva of the eye such that the implanted system components (e.g., the display 100 and the controller 300) do not break the immune barrier (e.g., percutaneous wires are not used). In a second embodiment, the controller 300 is located on or near the brain stem (e.g., such that the controller 300 can be physically connected to a display 100 implanted on the brain stem without the use of percutaneous wires). However, the controller 300 can be located elsewhere.

Figure 17:
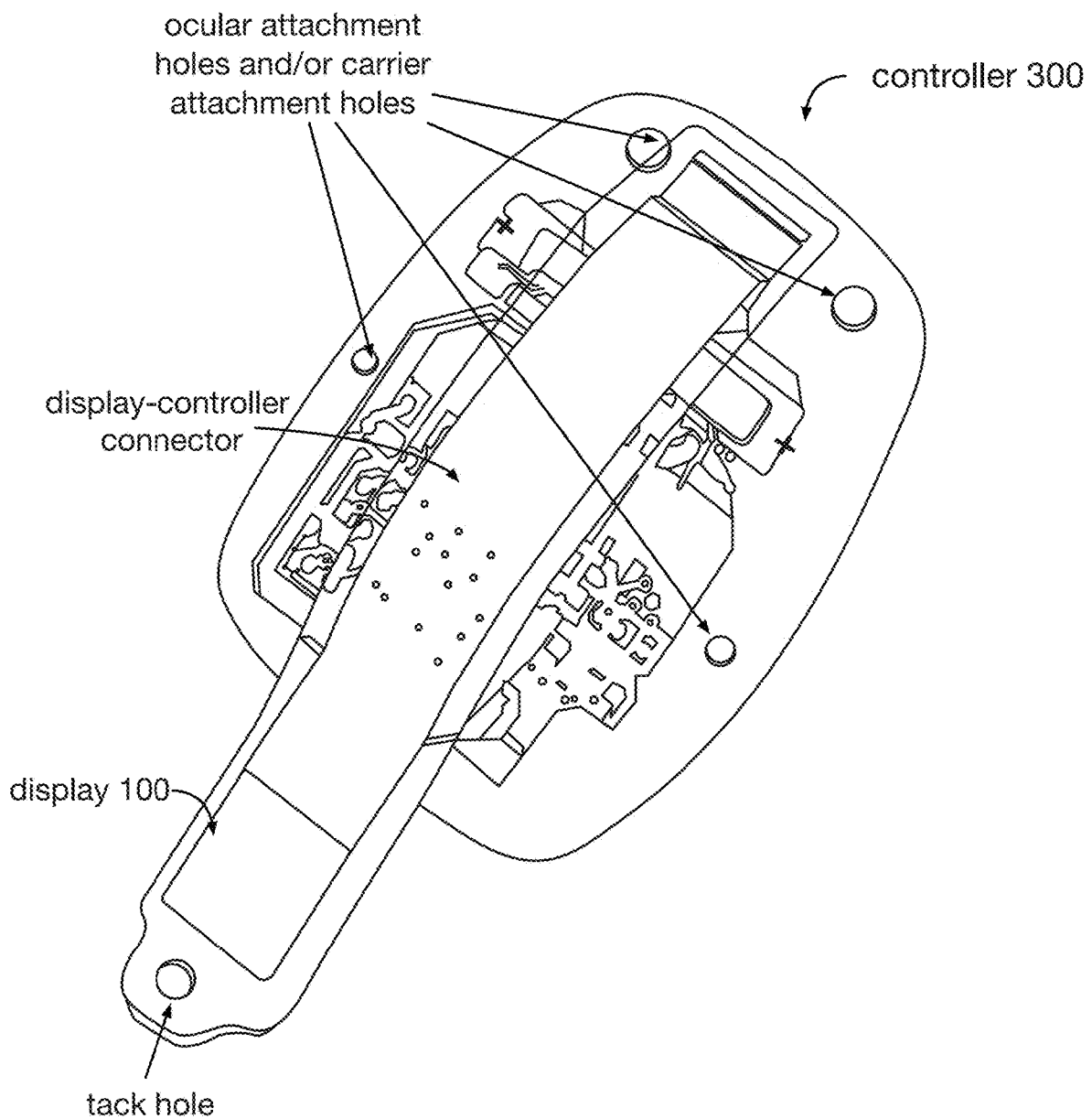
FIG. 17 depicts a second illustrative example of the system.

The controller 300 can optionally include an ocular attachment mechanism, which functions to attach the controller 300 to the outer surface of the eye (e.g., under the conjunctiva of the eye). In a specific example, the ocular attachment mechanism includes one or more suture attachments (e.g., suture holes, tabs, etc.). The ocular attachment mechanism can optionally include mechanisms used in glaucoma tube shunt implantation. The controller 300 can optionally include a carrier attachment mechanism, which functions to interface with a surgical carrier device used to facilitate implantation. The carrier attachment mechanism can include holes in the controller 300, ridges on the controller 300 (e.g., to interface with a clip), suture attachments, and/or any other securing mechanism. The carrier attachment mechanism can optionally include all or a subset of the ocular attachment mechanism (e.g., a subset of ocular attachment suture holes). An example is shown in FIG. 17.

However, the controller 300 can be otherwise configured.

The display 100, display-controller connector, controller 300, and/or any other implanted system components can be manufactured using a film (e.g., thin film) and optionally a secondary material (e.g., backing and/or an encapsulant), but can alternatively be otherwise manufactured. The film material can include titanium, platinum, gold, palladium, silicon, and/or any other metals. The thin film thickness can be between 50 nm-50 µm or any range or value therebetween (e.g., 100 nm-5 µm), but can alternatively be less than 50 nm or greater than 50 µm.

In a first variant, manufacturing the implanted system components includes integrated manufacturing of a monolithic thin film containing an array of excitation signal emission systems (e.g., array of µLEDs) and a display-controller connector (e.g., wiring). The monolithic thin film can additionally or alternatively include one or more electronics components of the controller 300 and/or connections therefor. In an example, the array of excitation signal emission systems and the display-controller connector can be manufactured using the same wafer. In examples, integrated manufacturing can enable fewer interfaces, improved component alignment, reduced thickness, increased component density (e.g., including wiring between µLEDs), reduced tolerance, and/or provide other advantages.

In a specific example, the implanted system components can be monolithically fabricated on epitaxially grown GaN-on-sapphire substrates, utilizing a polyimide and/or any other backing material as the flexible backbone for multilayer (e.g., 4-6 layers), through-via routing of traces (e.g., gold traces). Electronic components can optionally be assembled directly onto the polyimide-metal structures before substrate release. Individual µLEDs can optionally be buried in a monolithic polyimide package (e.g., as opposed to being transferred onto an existing routing layer). In variants, this can provide the advantage of high-resolution alignment on an inherently flexible substrate by building the flexible components onto the μLEDs and then releasing them afterwards. Additionally or alternatively, this can provide the advantage of denser routing and more tightly integrated packaging layers.

Figure 16:
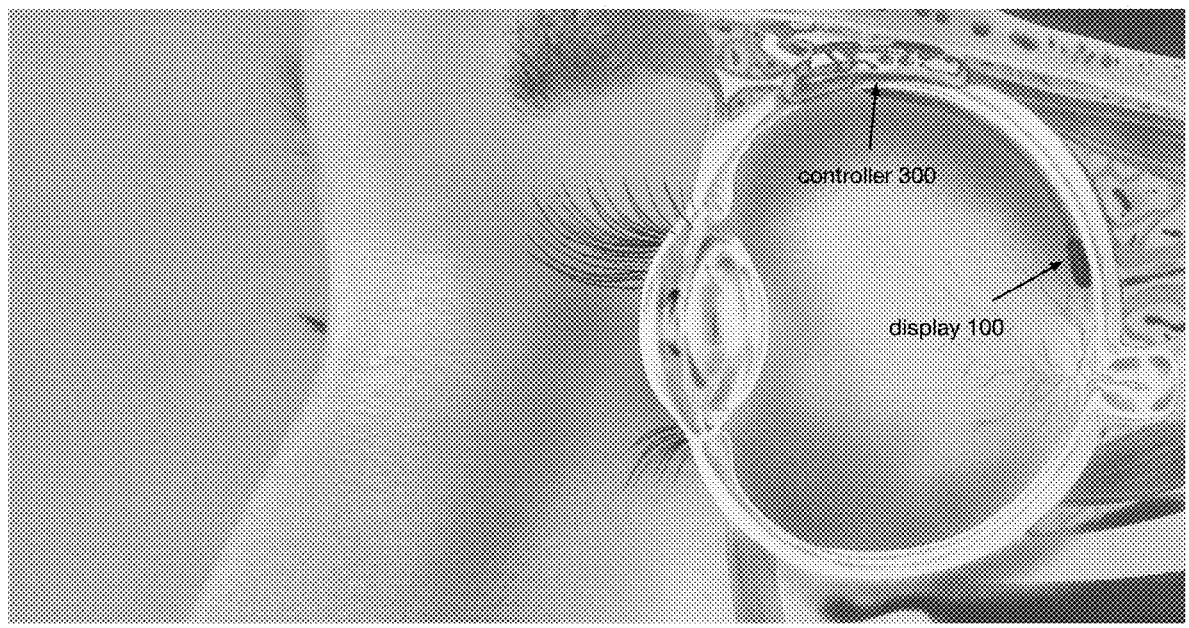
FIG. 16 depicts a first illustrative example of the system.
Figure 21A:
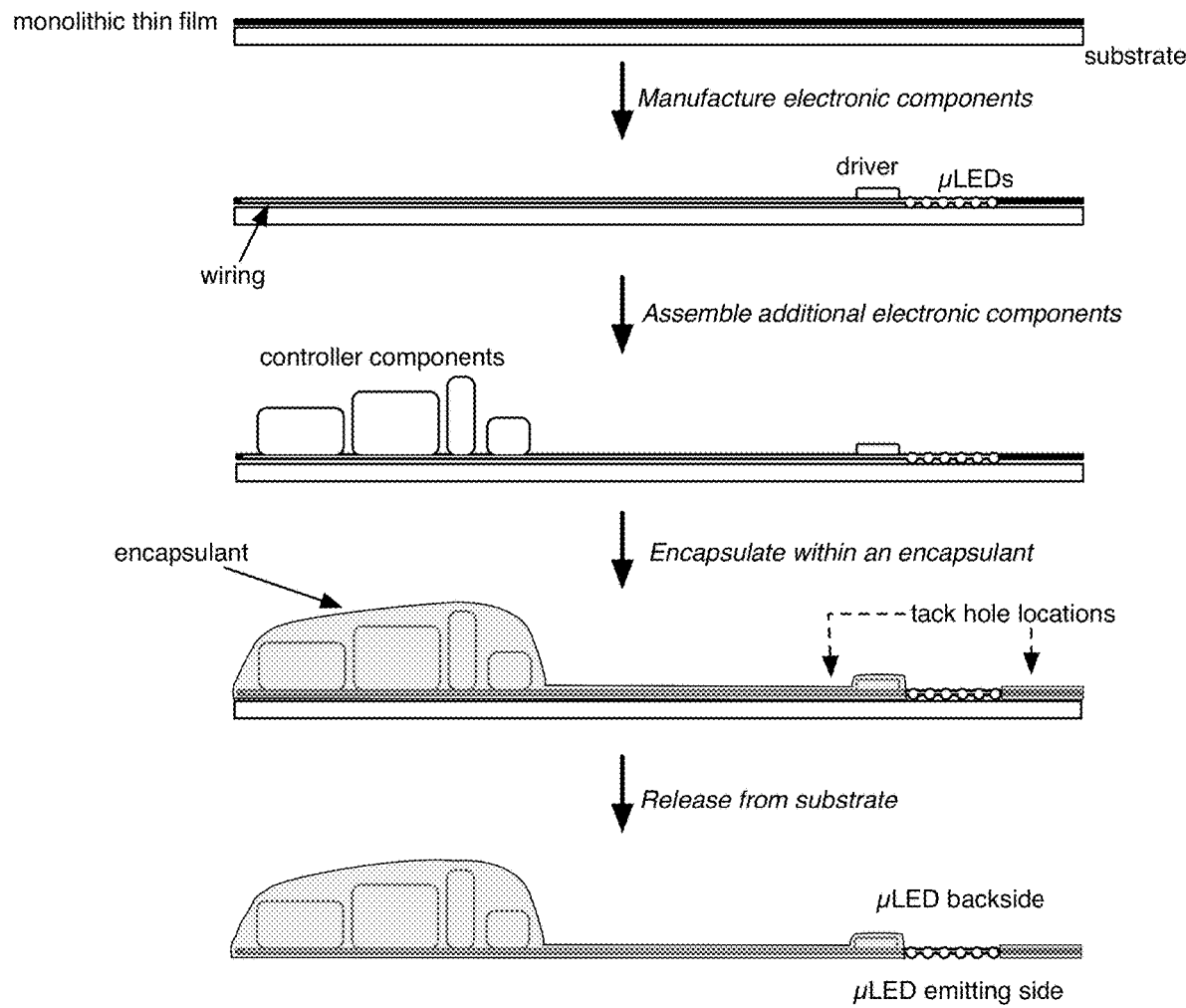
FIGS. 21A-21B depict examples of manufacturing system components.
Figure 21B:
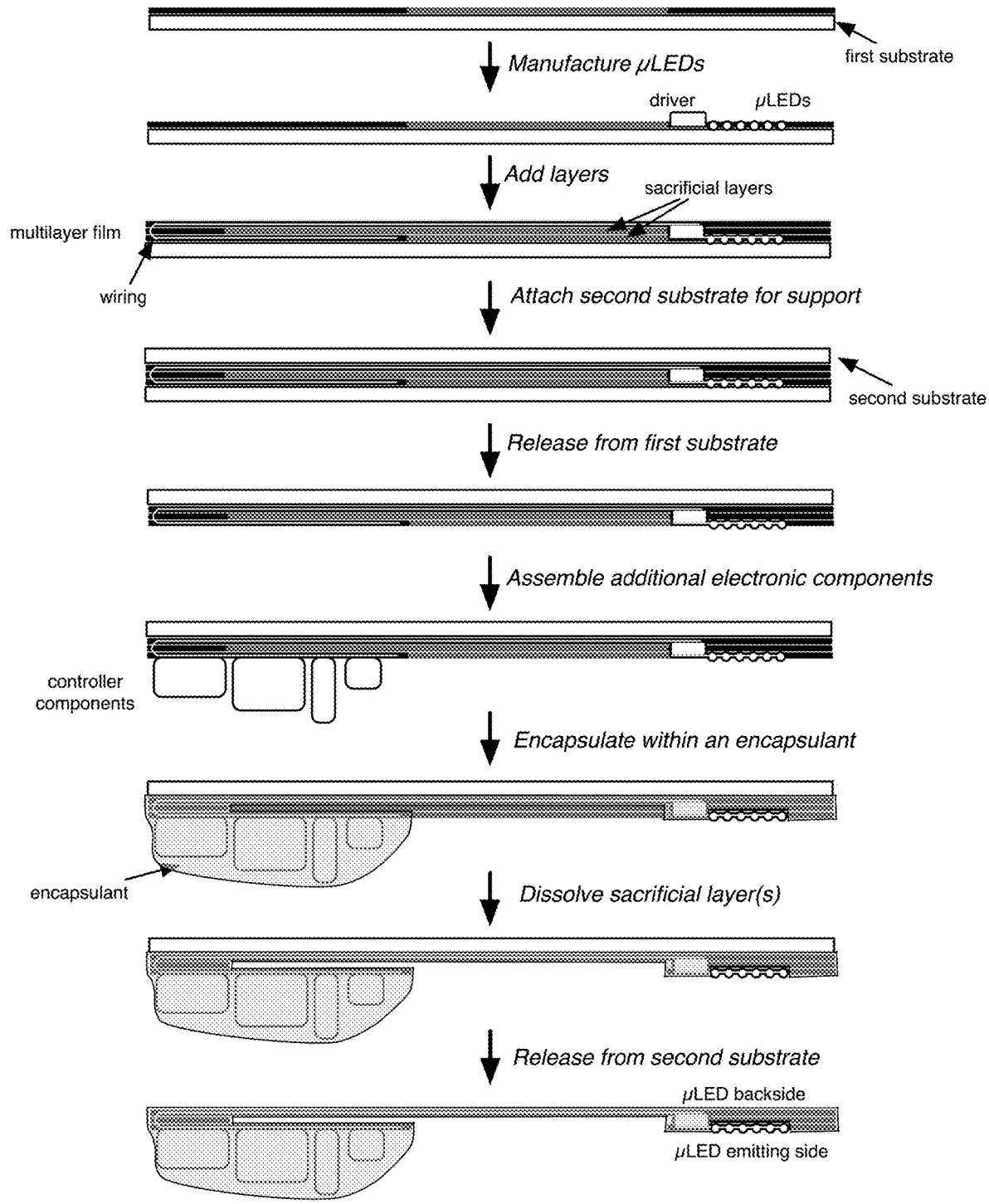
Figure 24A:
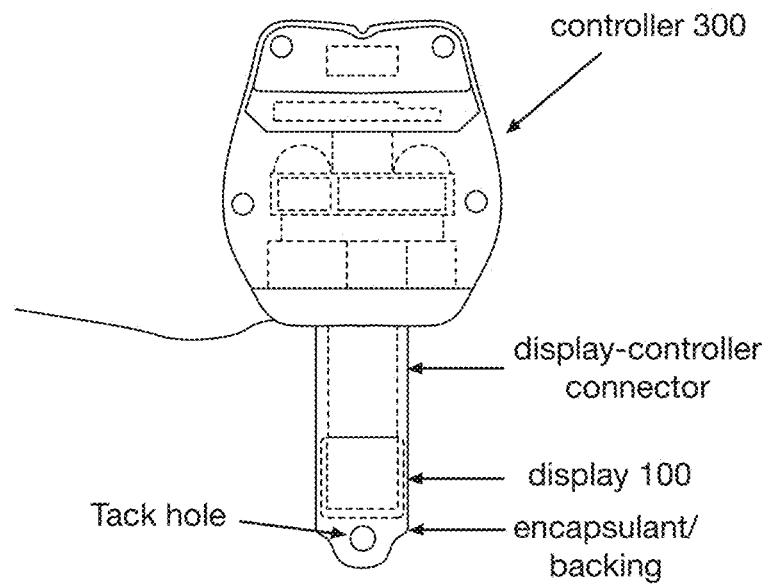
FIGS. 24A and 24B are example images of a system with a "hinge" display-controller connector configuration.
Figure 24B:
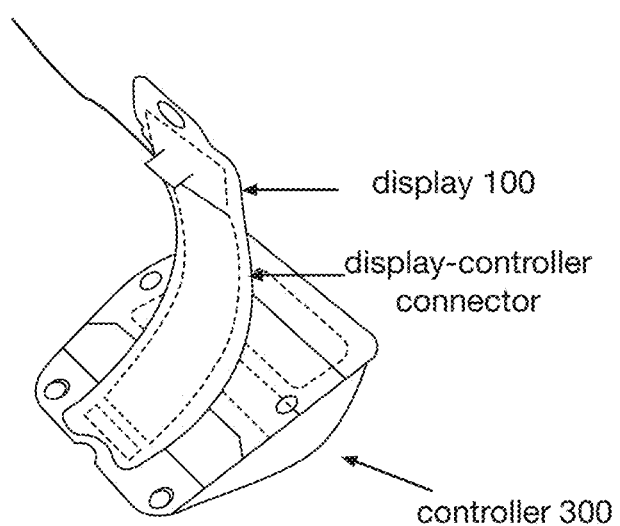
Figure 24C:
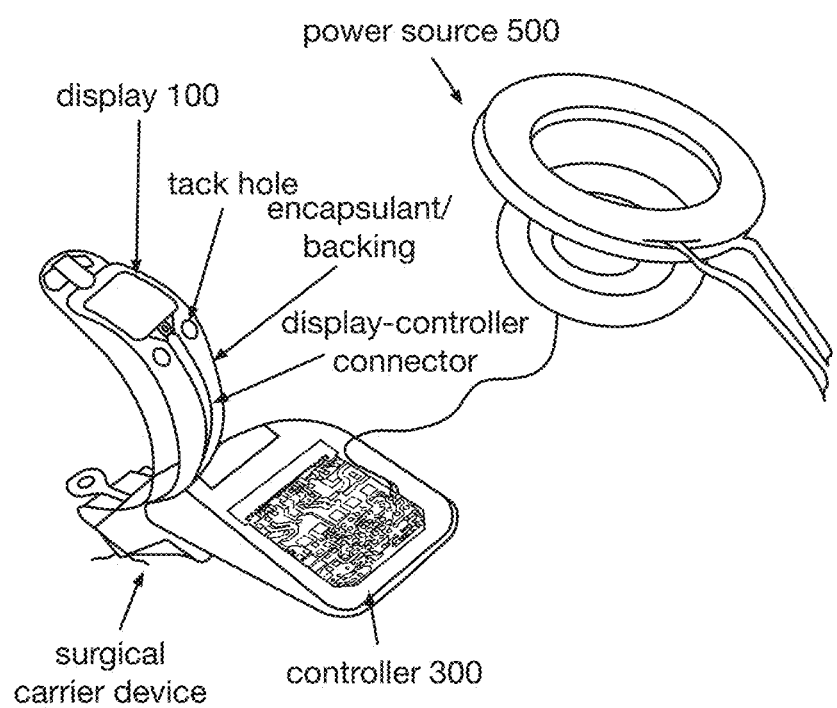
FIG. 24C is an example image of a system with a "u-turn" display-controller connector configuration.
Figure 25:
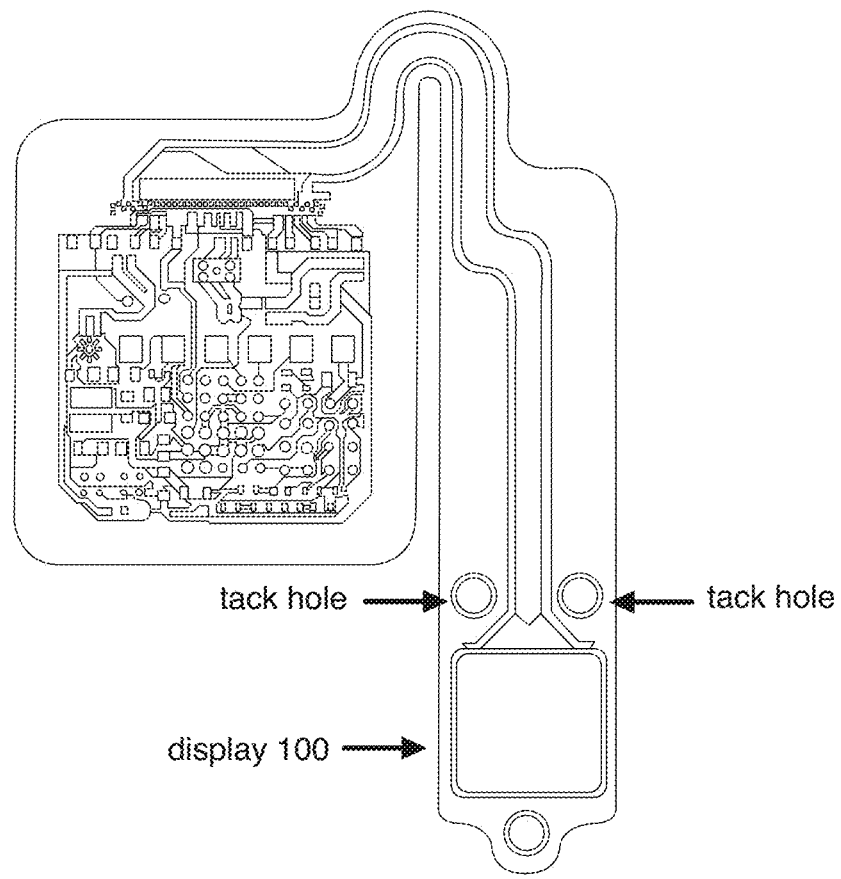
FIG. 25 is an image of the thin-film layer of a system with a "u-turn" display-controller connector configuration before bonding to controller components.

In a first example, the display 100 is manufactured using a monolithic multilayer film (e.g., adhered to a substrate). In an illustrative example, this multilayer film can appear as a single laminated film. In a first specific example, the display-controller connector can include connections routed in a substantially straight configuration (e.g., the μLED array is manufactured with the emitting side beneath a layer that includes the display-controller connections, wherein the controller components are assembled above the layer); an example is shown in FIG. 21A. In this example, the display-controller connector can be flexible such that the display-controller connector can bend when implanted (e.g., bend greater than 60°, greater than 90°, greater than 120°, greater than 150°, etc.); an example is shown in FIG. 16. In a second specific example, the display-controller connector can include connections routed in a "u-turn" configuration (e.g., the μLED array is manufactured with the emitting side above a layer that includes the display-controller connections, wherein the controller components are assembled above the layer); examples are shown in FIG. 24C and FIG. 25. In a second example, the display 100 is manufactured using a multilayer film (e.g., adhered to a substrate) including a sacrificial layer (e.g., partial or full layer) that is dissolved after tracing and/or other manufacturing processes are complete; an example is shown in FIG. 21B. The sacrificial layer can enable using two-dimensional manufacturing techniques to produce a 3D geometry, wherein the 3D geometry can better conform to the eye. The 3D geometry (e.g., a "hinge" configuration) can include a first flap (supporting the controller 300) that can be implanted on the outer surface of the eye and a second flap (supporting the display 100) that can be implanted inside the eye on the retina. Examples are shown in FIG. 17, FIG. 24A, and FIG. 24B.

In a second variant, manufacturing the display 100 includes separately manufacturing an array of excitation signal emission systems (e.g., on a thin film) and the display-controller connector. The array of excitation signal emission systems can optionally be assembled adjacent to additional electronic components (e.g., separately manufactured and then assembled on the film supporting the excitation signal emission system array using an interconnect layer). The additional electronic components can include drivers, transistors and/or other logic components, filters, signal sensor systems wiring between display components, and/or any other electronics. In examples, arranging the additional electronic components adjacent to the excitation signal emission systems can reduce the number of wires (the channel count) in the display-controller connector (e.g., less than 20, less than 10, etc.), increase flexibility of the display-controller connector, increase the wire diameter, increase the data bandwidth, reduce current loss, increase efficiency, and/or provide other advantages.

The display 100, display-controller connector, controller 300, and/or any other system components can optionally be attached to a backing (e.g., located on the backing, adhered to the backing, etc.) and/or encapsulated within an encapsulant (e.g., all implanted components are encapsulated in an encapsulant; the controller 300 is encapsulated in an encapsulant, while the display 100 and display-controller connector are adhered to a backing; the μLEDs are left unencapsulated while the driver and/or other system components are encapsulated; etc.). In a first example, the backing and/or encapsulant are rigid (e.g., sapphire). In a second example, the backing and/or encapsulant is flexible (e.g., a flexible polymer). Examples of backing and/or encapsulant materials include polyimide, liquid crystal polymer, parylene, elastomeric polyurethane, and/or any other suitable materials. The backing and/or encapsulant material can be biocompatible, flexible (e.g., at relevant thicknesses), water resistant, robust to surgical handling, have high adhesion strength for adhering to other display and/or backing and/or encapsulant materials, and/or have any other properties. The backing and/or encapsulant is preferably transparent or semi-transparent (e.g., such that the display 100 does not block any remaining photoreceptor function when the display 100 is implanted on a retina), but can alternatively be non-transparent (e.g., when the display 100 is implanted in the brain). The backing and/or encapsulant can optionally include an insulating material. For example, the insulation material can include a ceramic insulation material (e.g., silicon carbine, alumina, hafnia, etc.). The backing and/or encapsulant can optionally include a secondary cushioning material (e.g., epoxy underfill); example shown in FIG. 13A and FIG. 13B. For example, when backing and/or encapsulant includes rigid material, a soft polymer can be used to interface with the implantation location (e.g., retina). The cushioning material can optionally facilitate adhesion of the display 100 to the implantation location. The backing and/or encapsulant can optionally include a tab, wherein a surgeon can position the display 100 at or near the implantation location using the tab (e.g., by holding the tab with forceps).

Manufacturing optical components (e.g., microlens, back reflector, etc.) on the display 100 can optionally include: concurrently manufacturing the optical components during manufacturing of the array of excitation signal emission systems (e.g., engineered μLEDs are constructed with a parabolic geometry that functions as the optical component); adhering an optical component and/or an array of optical components (e.g., array of microlenses) to the display 100, backing, and/or encapsulant; manufacturing optical components on a (shared) substrate (e.g., wafer) with the excitation signal emission systems (e.g., wherein the optical components can be manufactured on the substrate before or after μLEDs are manufactured on the substrate); and/or using any other manufacturing technique.

In variants, the backing and/or encapsulant can be manufactured with engineered tension to facilitate implantation. For example, manufacturing the backing and/or encapsulant can include forming the backing and/or encapsulant material with a 3D geometry, such that, when implanted, the backing and/or encapsulant material exerts a spring force (e.g., biased radially outward) pressing the display 100 onto the implantation location (e.g., the retina). In a specific example, manufacturing the encapsulant can include encapsulating the display 100, display-controller connector, and/or any other system components within the encapsulant material while the system components are arranged in a specified 3D geometry. However, the backing and/or encapsulant can be otherwise manufactured.

However, the display 100, display-controller connector, controller 300, and/or other system components can be otherwise manufactured.

Figure 22:
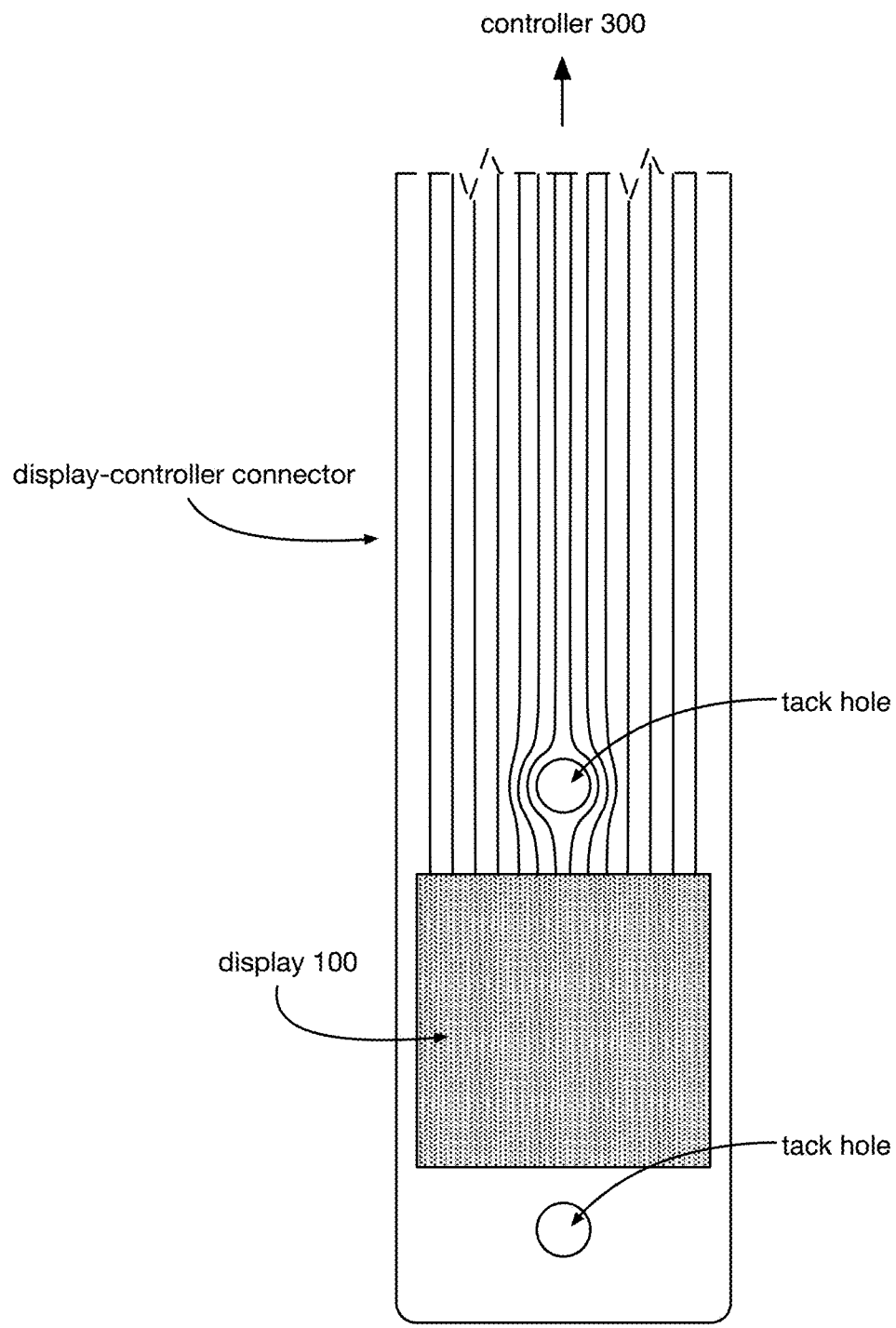
FIG. 22 depicts an example of tack holes.

The display 100, the display-brain interface 200, and/or the display-controller connector can be anchored (e.g., adhered, secured, etc.) to an implantation location. Anchoring methods can include: tissue adhesives, extrusions (e.g., 'spikes' of material) on the backing and/or encapsulant that act as anchors, packing, pressing the device against the implantation location (e.g., exchanging fluid in the eye for pressurized gas), tacks and/or pins inserted through a tack hole in the backing and/or encapsulant, inducing fibrotic growth around the device (e.g., via a laser), cell growth into or out of the display-brain interface, bracing the device against other tissue (e.g., connective tissue forming the eyeball), a combination thereof, and/or any other method. For example, the number of tacks can be between 1-5 or any range or value therebetween (e.g., 2-4), but can alternatively be greater than 5. In a specific example, a tack hole can be located on the display-controller connector (e.g., wherein the connections are routed around the tack hole; example shown in FIG. 22). In an illustrative example, implanting the display 100 and the controller 300, includes: making an incision in the eye (e.g., a sclerotomy), inserting the display 100 and the display-controller connector through the incision into the eye (e.g., using a surgical carrier device), anchoring the display 100 to the retina, and anchoring the controller 300 to the outside of the eye. Examples are shown in FIG. 19A, FIG. 19B, FIG. 19C, FIG. 28, and FIG. 29.

Figure 20A:
FIG. 20A depicts an illustrative example of an external device.
Figure 20B:
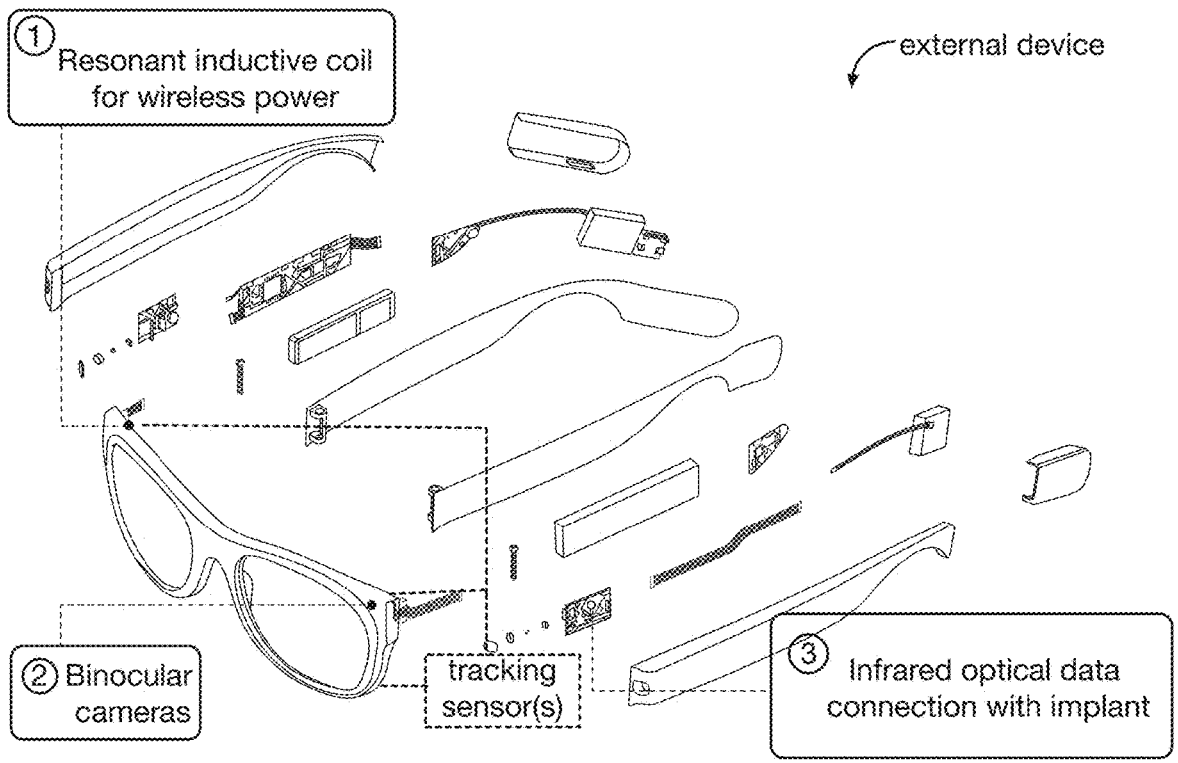
FIG. 20B depicts an exploded view of an illustrative example of an external device.

The system can be used with one or more external devices, which can function to: receive cell measurements (e.g., from the system), determine the controls (e.g., emission parameters) for the display 100, determine the pose of one or more implanted system components, and/or perform any other set of functionalities. Examples of external devices that can be used include: glasses, a contact lens, a hat, a personal computing device (e.g., smartphone, a laptop, etc.), a television, a combination thereof, and/or any other suitable external device. Examples are shown in FIG. 20A and FIG. 20B.

The external device 400 can optionally include: a communication element 420 configured to communicate with the system (e.g., communicate with a communication element of the controller 300), a processing system (e.g., processor, memory, etc.), a sensor 450, the power source 500 and/or component thereof, a tracking sensor, and/or any other set of components.

The communication element 420 of the external device is preferably complimentary to the controller's communication element(s) (e.g., communicate using the same wavelengths, such as IR, RF, etc.), but can be otherwise configured. The communication element 420 can include a transmitter, receiver, wired connections, and/or any other set of components. The communication element 420 is preferably not implanted in the user, but can alternatively be implanted in the user. The communication element 420 can be statically positioned relative to the controller 300 (e.g., the communication element 420 moves with the controller 300) or can move relative to the controller 300 (e.g., using beam steering and/or other methods to transmit data from the transmitter to the controller 300; wherein the controller moves as the eye moves and the communication element 420 remains stationary, etc.). Information transmitted by the communication element 420 can include: content (e.g., processed or unprocessed content), emission parameters (e.g., calculated based on the content), and/or any other information. Information received by the communication element 420 can include: cell measurements (e.g., cell states measured by the display 100), controller measurements (e.g., controller states measured by the controller sensor), a controller pose signal, a display pose signal, and/or any other information.

The optional tracking sensor can function to determine the pose of one or more components of the system (e.g., the controller 300, the display 100, etc.) and/or of the eye (e.g., the gaze of the eye). In a first variant, the tracking sensor includes a camera, which functions to track the eye (e.g., the eye pupil, a unique eye feature, the transfected cells, etc.) and/or a system component (e.g., the display 100 and/or controller 300 viewed through the eye; light backscattered by the display 100; etc.). In a second variant, the tracking sensor includes receiver configured to receive: light emitted and/or reflected from the one or more system components, a controller pose signal (e.g., a tracking signal or a pose estimation emitted via a controller communication element), a display pose signal (e.g., emitted via one or more excitation signal emission systems), and/or any other signal. In an example, the receiver includes a set of photodiodes (e.g., at least two photodiodes, at least three photodiodes, etc.), wherein the set of photodiodes can track light intensity of the signal. The external device 400 can optionally use a light propagation model (e.g., modeling light from the system component through the eye pupil) to localize the system component and/or the eye (e.g., the eye pupil) based on the tracking sensor measurements.

The external device 400 can optionally determine the content that is displayed. The content is preferably visual content, but can alternatively be any other content (e.g., content for other senses, such as temperature, other information not related to senses, etc.). Examples of content include: measurements of a real-world scene (e.g., adjacent the user, in front of the user or the external device 400, in the eye gaze direction, etc.); artificial reality (AR) overlays (e.g., only AR overlays); AR overlaid onto measurements of the adjacent real-world scene; virtual reality (VR); and/or any other information.

In a first variant, the content is measured using a sensor 450. Examples of the sensor 450 include: a camera (or any optics sensor), temperature sensor, motion sensor, pressure or force sensors, and/or any other sensor. The sensor 450 is preferably statically positioned relative to the external device 400 and/or components thereof (e.g., statically retained within a shared external device housing), but can alternatively move relative to the external device 400 (e.g., be separate from or move relative to the external device 400). In a first example, the sensor 450 is mounted to the user (e.g., via glasses, contact lens, hat, etc.), wherein the sensor can optionally move with user eye movement. In a second example, the sensor 450 is mounted separate from the user (e.g., on a drone, on a second user, a stationary camera in a secondary location, etc.). In a second variant, the content is generated using an AR engine, a VR engine, and/or any other content simulation method. In a third variant, the content is otherwise generated (e.g., content retrieved from a database, from another device, etc.).

The content optionally can be processed by the external device 400 (e.g., as part of generating emission parameters based on the content). For example, the content can be processed (e.g., temporal adjustments, spatial adjustments, intensity adjustments, etc.) such that the resultant signals received by the user from the display 100 is more natural (e.g., mapping an image to display excitation signal emissions such that the brain can better interpret signals in response to the light emissions). Content processing can be dependent on the display 100 implant location (e.g., processing an image for a retina display can be different from processing an image for direct neural stimulation), on the cell state, and/or on other parameters. In a first embodiment, processing the content includes adjusting the resolution. In a first specific example, an image can be compressed (e.g., downsampled) based on the number of cells in the display-brain interface 200 (e.g., optionally simulating the natural compression between photoreceptors and retinal ganglion cells). In a second specific example, content can be adjusted for variable resolution within the display 100 (e.g., a lower resolution at locations on the display 100 located further from the fovea). In a second embodiment, the content can be processed based on eye and/or eyelid movement. In a first example, the content can be based on an image sampled by a first sensor and an eye track determined using a second sensor (e.g., a motion sensor on the controller 300, a tracking sensor on the external device 400, a combination thereof, etc.), wherein the content is associated with a field of view of the eye based on the eye orientation. In a second example, content can be halted or otherwise adjusted when a user's eyelid is closed. In a third embodiment, content can be processed to account for image depth (e.g., to enable the brain to process a 2D image as a 3D image). In a third embodiment, content can be adjusted based on cell state (e.g., brightness increased when less than a threshold number of cells are stimulated; brightness decreased when more than a threshold number of cells are saturated; etc.).

However, the external device 400 can be otherwise configured.

The power source 500 functions to power one or more implanted system components (e.g., the controller 300 and/or the display 100). In a first variant, the power source 500 (or a component of the power source 500) is remote to the implanted system components. The power source 500 can include a power transmitter component remote to the implanted system components (e.g., coupled to the external device 400, coupled to a separate device, etc.) as well as a power receiver component connected to one or more implanted system components (e.g., coupled to the controller 300). For example, the power receiver component can be coupled to the controller 300 via a flexible tether (e.g., allowing for free positioning). In specific examples, power receiver components can include: a magnetic coil, a magnetoresistive film, and/or other power receiver components that can interface with an external induction power source. The power source 500 can provide power to the implanted system components via induction, IR, RF, and/or any other remote power method. The power source 500 and/or components thereof can be located in the same or a different external device as the communication element 420 (e.g., the power source 500 is located on a pair of glasses with the communication element 420). The implanted system components preferably do not have substantial power storage components such that the implanted system components are not fully operational without power from the power source 500 (e.g., when the power source 500 is located on a pair of glasses, power is halted to the (implanted) controller 300 and/or display 100 when the glasses are removed from the user), but can alternatively have power storage. In a second variant, the power source 500 is implanted with the system components (e.g., a battery implant).

The power consumption of the implanted system components can be between 10 mW-100 mW or any range or value therebetween (e.g., 30 mW-35 mW, less than 50 mW, etc.), but can alternatively be greater than 10 mW or less than 100 mW.

However, the power source 500 can be otherwise configured.

In variants, the system can use system and methods disclosed in: "A thin-film optogenetic visual prosthesis" (Knudsen E B, Zappitelli K, Brown J, Reeder J, Smith K S, Rostov M, Choi J, Rochford A, Slager N, Miura S K, Rodgers K, Reed A, Israeli Y R L, Shiraga S, Seo K J, Wolin C, Dawson P, Eltaeb M, Dasgupta A, Chong P, Charles S, Stewart J M, Silva R A, Kim T, Kong Y, Mardinly A R, Hodak M. 2023. bioRxiv doi: 10.1101/2023.01.31.526482), which is incorporated in its entirety by this reference.

Illustrative Examples

In a first illustrative example, the system can function as a visual prosthesis for a user who has lost function of their photoreceptors, but still has functional retinal ganglion cells. The external device 400 transmits an image (e.g., sampled by a camera) and/or emission parameters determined based on the image to the controller 300, wherein the controller 300 controls the display 100 based on the received information. Light emission systems in the display 100 emit light based on the emission parameters and/or other control information. The light is received by native retinal ganglion cells of the user (the display-brain interface 200), wherein the retinal ganglion cells are genetically modified to express transgenic proteins sensitive to the light emission wavelength. The retinal ganglion cells stimulate neurons in the brain in response to receiving the light, wherein the brain can interpret the stimulation (e.g., enabling the user to 'see' the image).

In a second illustrative example, the system can function as a visual prosthesis for a user who has lost function of their photoreceptors and/or retinal ganglion cells. The controller 300 provides emission parameters, determined based on a received image, to the display 100, wherein light emission systems in the display 100 emit light based on the emission parameters. The light is received by genetically modified cells (e.g., genetically modified to express transgenic proteins sensitive to the light emission wavelength) seeded into a cell support connected to the display 100. The genetically modified cells interface with native cells (e.g., using axons and/or dendrites) to provide a signal to the native cells that ultimately provides a signal to the brain. In a specific example, the genetically modified cells in the cell support stimulate native retinal ganglion cells (e.g., wherein the native retinal ganglion cells are functional). In a second specific example, the genetically modified cells in the cell support function as retinal ganglion cells and directly stimulate the brain.

In a third illustrative example, the system can function as a retina display (e.g., for an artificial reality system) for user who has functional photoreceptors and retinal ganglion cells. The controller 300 provides emission parameters, determined based on a generated image, to the display 100, wherein light emission systems in the display 100 emit light based on the emission parameters. The light emissions include multiple wavelengths of light (e.g., RBG wavelengths) and is received by native retinal ganglion cells of the user (the display-brain interface 200), wherein the retinal ganglion cells are not genetically modified. The retinal ganglion cells stimulate neurons in the brain in response to receiving the light, wherein the brain can interpret the stimulation.

In a fourth illustrative example, the system can function to directly stimulate neurons, enabling the brain to receive and interpret any type of content (e.g., visual and/or non-visual content, simulated and/or measured information, etc.). The controller 300 provides emission parameters, determined based on received content, to the display 100 (implanted in the brain, brain stem, spinal cord, or other nervous system component), wherein light emission systems in the display 100 emit light based on the emission parameters. The light is received by genetically modified cells (e.g., genetically modified to express transgenic proteins sensitive to the light emission wavelength) seeded into a cell support connected to the display 100. The genetically modified cells interface with native neurons (e.g., using axons and/or dendrites) to provide a signal directly to the brain.

Different subsystems and/or modules discussed above can be operated and controlled by the same or different entities. In the latter variants, different subsystems can communicate via: APIs (e.g., using API requests and responses, API keys, etc.), requests, and/or other communication channels.

Alternative embodiments implement the above methods and/or processing modules in non-transitory computer-readable media, storing computer-readable instructions that, when executed by a processing system, cause the processing system to perform the method(s) discussed herein. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-transitory computer readable media, or any suitable device. The computer-executable component can include a computing system and/or processing system (e.g., including one or more collocated or distributed, remote or local processors) connected to the non-transitory computer-readable medium, such as CPUs, GPUs, TPUS, microprocessors, or ASICs, but the instructions can alternatively or additionally be executed by any suitable dedicated hardware device.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

As a person skilled in the art will recognize from the previous detailed description and from the figures and claims, modifications and changes can be made to the preferred embodiments of the invention without departing from the scope of this invention defined in the following claims.

We claim:

1. A system, comprising:
   a controller, wherein the controller is configured to couple to an outer surface of an eye of a user, the controller comprising:
      a receiver configured to receive content from an external device; and
      a processor configured to determine display instructions based on the content;
      a connector comprising a plurality of electronic connections configured to transmit the display instructions from the controller to a display;
   a sensor configured to be implanted in the user, wherein the sensor is configured to measure a cell state of a cell of interest in genetically modified cells in a retina of the user, wherein the cell state comprises one of a current or a voltage, wherein the display instructions are adjusted based on measurements from the sensor, wherein the measurements comprise the cell state, wherein the display instructions are adjusted based on the cell state; and
   the display, wherein the display is configured to couple to the retina of the user, the display comprising:
      an array of μLEDs configured to emit light signals according to the display instructions, wherein the light signals are receivable by the genetically modified cells in the retina.

2. The system of claim 1, wherein the genetically modified cells are transfected with a gene for a light-sensitive protein, wherein the genetically modified cells produce biochemical signals in response to receiving the light signals.

3. The system of claim 2, wherein the genetically modified cells comprise retinal ganglion cells.

4. The system of claim 1, wherein the display instructions comprise a timeseries of light array patterns, wherein each light array pattern comprises light intensity parameters, wherein each light array pattern encodes a frame of the content.

5. The system of claim 1, wherein the display further comprises logic components, wherein the display instructions comprise μLED state change instructions.

6. The system of claim 1, wherein the system is manufactured using monolithic integration on a thin film.

7. The system of claim 1, wherein the array of μLEDs is configured to emit light signals with a fixed wavelength.

8. The system of claim 7, wherein the fixed wavelength is between 510 nm and 550 nm.

9. The system of claim 1, wherein the display further comprises a microoptical component configured to collimate the light signals.

10. The system of claim 9, wherein the microoptical component comprises one of a microlens, a metalens, or a back reflector.

11. The system of claim 1, wherein each μLED is configured to emit a light signal receivable by less than 20 of the genetically modified cells in the retina.

12. The system of claim 1, wherein the content comprises an image, wherein the external device comprises glasses and a camera configured to sample the image.

13. The system of claim 1, wherein adjusting the display instructions comprises one of increasing or decreasing an intensity of a light signal emitted by a μLED in the array of μLEDs, the μLED corresponding to the cell of interest.

* * * * *